(12) United States Patent
Lo et al.

(10) Patent No.: US 9,778,164 B2
(45) Date of Patent: Oct. 3, 2017

(54) FLUIDIC FLOW CYTOMETRY DEVICES AND PARTICLE SENSING BASED ON SIGNAL-ENCODING

(71) Applicant: The Regents of the University of California, Oakland, CA (US)

(72) Inventors: Yu-Hwa Lo, San Diego, CA (US); Chun Hao Randy Chen, Arcadia, CA (US); Sung Hwan Cho, La Jolla, CA (US); Shang-Feng Tsai, Sunnyvale, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/853,765

(22) Filed: Sep. 14, 2015

(65) Prior Publication Data

US 2016/0003729 A1    Jan. 7, 2016

Related U.S. Application Data

(63) Continuation of application No. 13/254,851, filed as application No. PCT/US2010/026884 on Mar. 10, 2010, now Pat. No. 9,134,221.

(Continued)

(51) Int. Cl.
*G01N 15/14* (2006.01)
*G01N 15/00* (2006.01)
*G01N 15/10* (2006.01)

(52) U.S. Cl.
CPC ..... *G01N 15/1434* (2013.01); *G01N 15/1425* (2013.01); *G01N 15/1459* (2013.01);
(Continued)

(58) Field of Classification Search
CPC ........... G01N 15/1459; G01N 15/1427; G01N 15/1429; G01N 15/1434; G01N 15/147; G01N 2015/1006; G01N 2015/149; G01N 2015/0065; G01N 2015/1402; G01N 2015/144; G01N 2015/1477;
(Continued)

(56) References Cited

U.S. PATENT DOCUMENTS

| 3,790,760 A | 2/1974 | Stiller |
| 3,984,307 A * | 10/1976 | Kamentsky ............. B07C 5/342 |
| | | 209/546 |
| 5,917,733 A | 6/1999 | Bangham |
| 6,049,381 A | 4/2000 | Reintjes et al. |
| 6,139,800 A | 10/2000 | Chandler |
| 6,744,038 B2 | 6/2004 | Wang et al. |
| 6,778,724 B2 | 8/2004 | Wang et al. |
| 6,784,420 B2 | 8/2004 | Wang et al. |
| 6,815,664 B2 | 11/2004 | Wang et al. |

(Continued)

FOREIGN PATENT DOCUMENTS

| EP | 2531832 A2 | 12/2012 |
| EP | 2671065 A1 | 12/2013 |

(Continued)

OTHER PUBLICATIONS

Cho, Sung Hwan, et al., "Microfluidic Photonic Integrated Circuits," Nov. 18, 2008, Optoelectronic Materials and Devices III, Proc. of SPIE vol. 7135, pp. 71350M1-71350M10.*

(Continued)

*Primary Examiner* — Gordon J Stock, Jr.
(74) *Attorney, Agent, or Firm* — Perkins Coie LLP

(57) ABSTRACT

Microfluidic devices, systems and techniques in connection with particle sorting in liquid, including cytometry devices and techniques and applications in chemical or biological testing and diagnostic measurements.

29 Claims, 30 Drawing Sheets

Related U.S. Application Data

(60) Provisional application No. 61/262,787, filed on Nov. 19, 2009, provisional application No. 61/158,969, filed on Mar. 10, 2009.

(52) U.S. Cl.
CPC . *G01N 15/1484* (2013.01); *G01N 2015/0065* (2013.01); *G01N 2015/1006* (2013.01); *G01N 2015/145* (2013.01); *G01N 2015/149* (2013.01); *G01N 2015/1415* (2013.01); *G01N 2015/1447* (2013.01)

(58) Field of Classification Search
CPC ... G01N 2015/1486; G01N 2015/1493; G01N 21/6486; G01N 35/00732; G01N 2015/14; G01N 2015/1404; G01N 2015/1406; G01N 2015/1409; G01N 2015/1411; G01N 2015/1413; G01N 2015/1415; G01N 2015/1418; G01N 2015/142; G01N 2015/1422; G01N 2015/1434; G01N 2015/1438; G01N 2015/1454; G01N 2015/1443; G01N 2015/1445; G01N 2015/1447; G01N 2015/145; G01N 2015/1452; G01N 2015/1456; G01N 2015/1461; G01N 2015/1463; G01N 2015/1465; G01N 2015/1468; G01N 2015/1472; G01N 2015/1479; G01N 2015/1481; G01N 2015/1488; G01N 2015/1495; G01N 2015/1497; G01N 15/14; G01N 15/1425; G01N 15/1484; G06K 19/06009; G06K 19/06046

See application file for complete search history.

(56) References Cited

U.S. PATENT DOCUMENTS

| | | | |
|---|---|---|---|
| 6,833,542 B2 | 12/2004 | Wang et al. | |
| 6,909,824 B1 | 6/2005 | Messica et al. | |
| 6,936,811 B2 | 8/2005 | Kibar | |
| 7,068,874 B2 | 6/2006 | Wang et al. | |
| 7,157,271 B2 | 1/2007 | Ryu et al. | |
| 7,160,687 B1 | 1/2007 | Kapur et al. | |
| 7,245,379 B2 | 7/2007 | Schwabe | |
| 7,298,478 B2 | 11/2007 | Gilbert et al. | |
| 7,355,699 B2 | 4/2008 | Gilbert et al. | |
| 7,492,522 B2 | 2/2009 | Gilbert et al. | |
| 7,576,861 B2 | 8/2009 | Gilbert et al. | |
| 7,701,580 B2 | 4/2010 | Bassler et al. | |
| 7,745,221 B2 | 6/2010 | Butler et al. | |
| 7,746,466 B2 | 6/2010 | Godin et al. | |
| 7,767,444 B2 | 8/2010 | Liu et al. | |
| 7,870,964 B2 | 1/2011 | Gilbert et al. | |
| 8,026,054 B2 | 9/2011 | Sharma et al. | |
| 8,270,781 B2 | 9/2012 | Lo et al. | |
| 8,277,764 B2 | 10/2012 | Gilbert et al. | |
| 8,373,860 B2 | 2/2013 | Kiesel et al. | |
| 8,426,209 B2 | 4/2013 | Butler et al. | |
| 8,629,981 B2 | 1/2014 | Martini et al. | |
| 8,691,164 B2 | 4/2014 | Butler et al. | |
| 8,822,207 B2 | 9/2014 | Foster et al. | |
| 8,993,311 B2 | 3/2015 | Foster et al. | |
| 9,011,797 B2 | 4/2015 | Gilbert et al. | |
| 9,134,221 B2 * | 9/2015 | Lo | G01N 15/1459 |
| 2002/0011097 A1 | 1/2002 | Kuderer et al. | |
| 2002/0108859 A1 | 8/2002 | Wang et al. | |
| 2002/0113204 A1 | 8/2002 | Wang et al. | |
| 2002/0115163 A1 | 8/2002 | Wang et al. | |
| 2002/0121443 A1 | 9/2002 | O'Connell | |
| 2002/0122167 A1 | 9/2002 | Riley et al. | |
| 2002/0123112 A1 | 9/2002 | Wang et al. | |
| 2002/0137059 A1 | 9/2002 | Wu et al. | |
| 2002/0160470 A1 | 10/2002 | Zhang | |
| 2003/0124516 A1 | 7/2003 | Chung et al. | |
| 2003/0137666 A1 | 7/2003 | Johnson | |
| 2003/0159999 A1 * | 8/2003 | Oakey | B01D 57/02 210/695 |
| 2003/0194755 A1 | 10/2003 | Schnabel et al. | |
| 2003/0211461 A1 | 11/2003 | Kariv et al. | |
| 2003/0215791 A1 | 11/2003 | Garini et al. | |
| 2004/0009540 A1 | 1/2004 | Soohoo et al. | |
| 2004/0023310 A1 | 2/2004 | Kariv et al. | |
| 2004/0033539 A1 | 2/2004 | Schnabel et al. | |
| 2004/0053209 A1 | 3/2004 | Kariv et al. | |
| 2004/0072278 A1 | 4/2004 | Chou et al. | |
| 2004/0161772 A1 * | 8/2004 | Bohm | B07C 5/34 435/6.16 |
| 2005/0036139 A1 | 2/2005 | Johnson | |
| 2005/0068536 A1 | 3/2005 | Schwabe | |
| 2005/0105077 A1 | 5/2005 | Padmanabhan et al. | |
| 2005/0112541 A1 | 5/2005 | Durack et al. | |
| 2005/0164372 A1 | 7/2005 | Kibar | |
| 2006/0060767 A1 | 3/2006 | Wang et al. | |
| 2006/0066837 A1 | 3/2006 | Ortyn et al. | |
| 2006/0117563 A1 | 6/2006 | Sugahara | |
| 2006/0192955 A1 | 8/2006 | Jorgenson et al. | |
| 2006/0197033 A1 | 9/2006 | Hairston et al. | |
| 2006/0282752 A1 | 12/2006 | Kuroda | |
| 2007/0086918 A1 | 4/2007 | Hartley et al. | |
| 2007/0117086 A1 | 5/2007 | Evans et al. | |
| 2007/0140638 A1 | 6/2007 | Yang et al. | |
| 2007/0159627 A1 | 7/2007 | Johnson | |
| 2008/0233635 A1 | 9/2008 | Evans et al. | |
| 2008/0302732 A1 * | 12/2008 | Soh | B01L 3/502761 210/695 |
| 2008/0319680 A1 | 12/2008 | Fox et al. | |
| 2009/0027666 A1 | 1/2009 | Godin et al. | |
| 2009/0042737 A1 | 2/2009 | Katz et al. | |
| 2009/0155832 A1 | 6/2009 | Lo et al. | |
| 2009/0190121 A1 | 7/2009 | Hegyi et al. | |
| 2009/0194705 A1 | 8/2009 | Kiesel et al. | |
| 2009/0195773 A1 | 8/2009 | Bassler et al. | |
| 2010/0018310 A1 | 1/2010 | Mutharasan et al. | |
| 2010/0051828 A1 | 3/2010 | Doemer et al. | |
| 2010/0108577 A1 | 5/2010 | Wang et al. | |
| 2010/0117007 A1 | 5/2010 | Kibar | |
| 2010/0155572 A1 | 6/2010 | Kiesel et al. | |
| 2011/0039258 A1 | 2/2011 | McNeeley et al. | |
| 2011/0086769 A1 | 4/2011 | Oliphant et al. | |
| 2011/0196637 A1 | 8/2011 | Sharpe et al. | |
| 2012/0009619 A1 | 1/2012 | Gilbert et al. | |
| 2012/0012508 A1 | 1/2012 | Deshpande et al. | |
| 2012/0045763 A1 | 2/2012 | Sharma et al. | |
| 2012/0077191 A1 | 3/2012 | Gunning et al. | |
| 2012/0078531 A1 | 3/2012 | Lo et al. | |
| 2012/0138513 A1 | 6/2012 | Johnson et al. | |
| 2012/0190105 A1 | 7/2012 | Foster et al. | |
| 2012/0202237 A1 | 8/2012 | Sedoglavich et al. | |
| 2012/0255373 A1 | 10/2012 | Foster et al. | |
| 2012/0261013 A1 | 10/2012 | Gilbert et al. | |
| 2012/0277902 A1 | 11/2012 | Sharpe et al. | |
| 2012/0307244 A1 | 12/2012 | Sharpe et al. | |
| 2013/0004987 A1 | 1/2013 | Lo et al. | |
| 2013/0016335 A1 | 1/2013 | Lo et al. | |
| 2013/0083315 A1 | 4/2013 | Lo et al. | |
| 2013/0171683 A1 | 7/2013 | Durack et al. | |
| 2013/0313170 A1 | 11/2013 | Bohm et al. | |
| 2013/0334407 A1 | 12/2013 | Perrault, Jr. et al. | |
| 2014/0251879 A1 | 9/2014 | Deshpande et al. | |
| 2015/0211979 A1 * | 7/2015 | Lo | G01N 15/1459 356/338 |
| 2016/0003729 A1 | 1/2016 | Lo et al. | |

FOREIGN PATENT DOCUMENTS

| | | |
|---|---|---|
| EP | 2872887 A1 | 5/2015 |
| WO | 9405775 A4 | 3/1994 |
| WO | 02059577 | 8/2002 |
| WO | 2007051170 A2 | 5/2007 |

(56) References Cited

FOREIGN PATENT DOCUMENTS

| WO | 2010104993 A2 | 9/2010 |
|---|---|---|
| WO | 2012083250 A2 | 6/2012 |
| WO | 2012106645 A1 | 8/2012 |
| WO | 2012154614 A1 | 11/2012 |
| WO | 2013010134 A2 | 1/2013 |
| WO | 2013192342 A1 | 12/2013 |

OTHER PUBLICATIONS

Chen, C.H., et al., "High-Throughput Cell Sorter With Piezoelectric Actuation," Oct. 12-16, 2008, Twelfth International Conference on Miniaturized Systems for Chemistry and Life Sciences in San Diego, California, USA, pp. 155-157.*

Chen, C., et al., "Microfluidic cell sorter with integrated piezoelectric actuator," Biomedical Microdevices, 11(6):1223-1231, Aug. 2009.

Cho, S., et al., "Micro-fabricated Fluorescence-Activated Cell Sorter," Annual International Conference of the IEEE Engineering in Medicine and Biology Society, pp. 1075-1078, Sep. 3-6, 2009.

Cho, S., et al., "Microfluidic Photonic Integrated Circuits," Optoelectronic Materials and Devices, vol. 7135, pp. 1-17, Jan. 2008.

Cho, S., et al., "Optofluidic Waveguides in Teflon AF-Coated PDMS Microfluidic Channels," IEEE Photonics Technology Letters, 21(15)1057-1059, Aug. 1, 2009.

Fu, A.Y., et al., A Microfabricated Fluorescence-Activated Cell Sorter, Nature Biotechnology, vol. 17 pp. 1109-1111, Nov. 1999.

Godin, J., et al., "Microfluidics and photonics for Bio-System-on-a-Chip: A review of advancements in technology towards a microfluidic flow cytometry chip," Journal of Biophotonics, 1(5):355-376, Oct. 2008.

International Search Report and Written Opinion mailed on Nov. 1, 2007 for International Application No. PCT/US2006/060313, filed Oct. 27, 2006 (4 pages).

International Search Report and Written Opinion mailed on Oct. 26, 2010 for International Application No. PCT/US2010/026884, filed Mar. 10, 2010 (10 pages).

Lee, G.-B., et al., "Micro Flow Cytometers with Buried SU-8/SOG Optical Waveguides," Sensors and Actuators A: Physical, 103(1):165-170, Jan. 2003.

Lien, V., et al., "Fluidic Photonic Integrated Circuit for In-Line Detection," Applied Physics Letters, 87(19):194106(1-3), Nov. 2005.

Lien, V., et al., "High-Sensitivity Cytometric Detection Using Fluidic-Photonic Integrated Circuits with Array Waveguides," IEEE Journal of Selected Topics in Quantum Electronics, 11(4):827-834, Jul./Aug. 2005.

Lien, V., et al., "Microfluidic-photonic-dielectrophoretic integrated circuits for biophotonic sensing," The 17th Annual Meeting of the IEEE Lasers and Electro-Optics Society, vol. 2, pp. 533-534, Nov. 2004.

Tung, Y.-C., et al., "PDMS-based opto-fluidic micro flow cytometer with two-color, multi-angle fluorescence detection capability using PIN photodiodes," Sensors and Actuators B, 98(2-3):356-367, Mar. 2004.

Lien, V., et al., "A Prealigned Process of Integrating Optical Waveguides With Microfluidic Devices," IEEE Photonics Technology Letters, 16(6):1525-1527, Jun. 2004.

Zhang, H., et al., "Time-of-Flight Optophoresis Analysis of Live Whole Cells in Microfluidic Channels," Biomedical Microdevices, 6(1):11-21, Mar. 2004.

\* cited by examiner

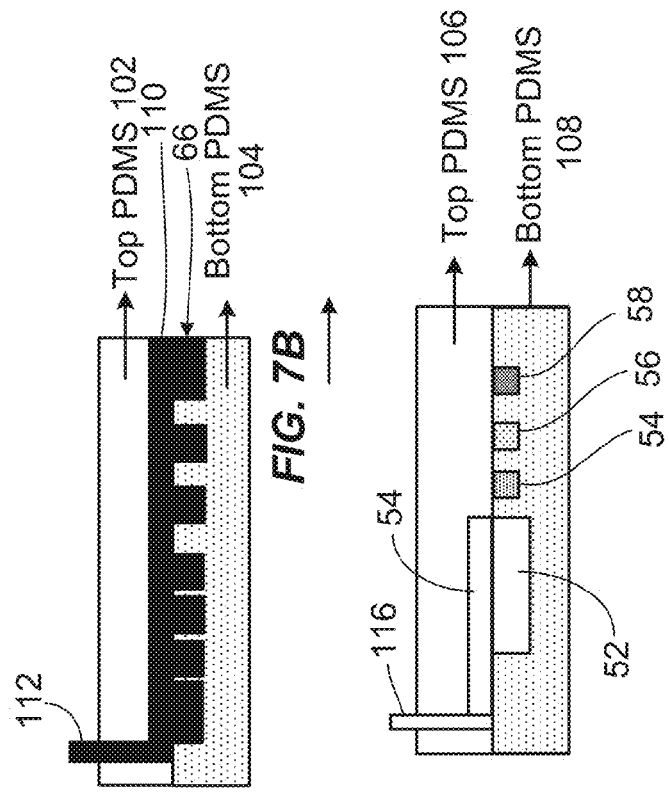
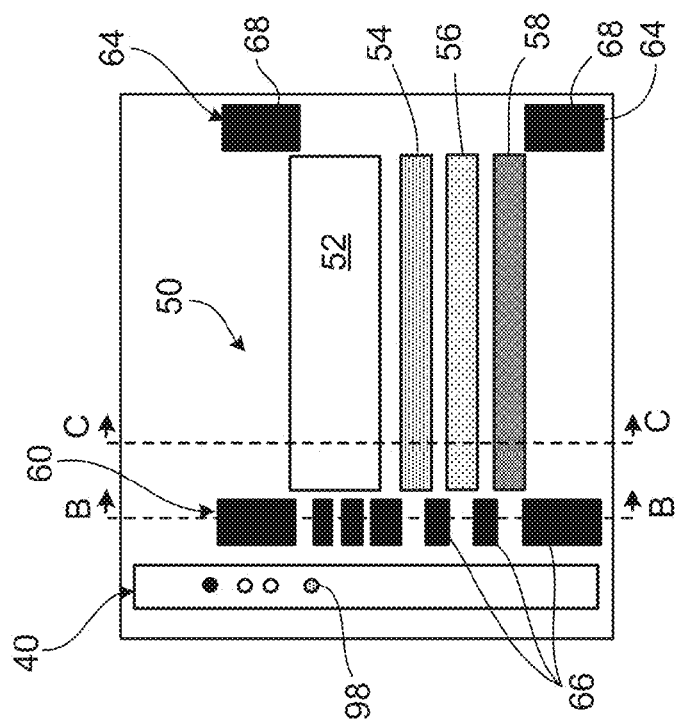

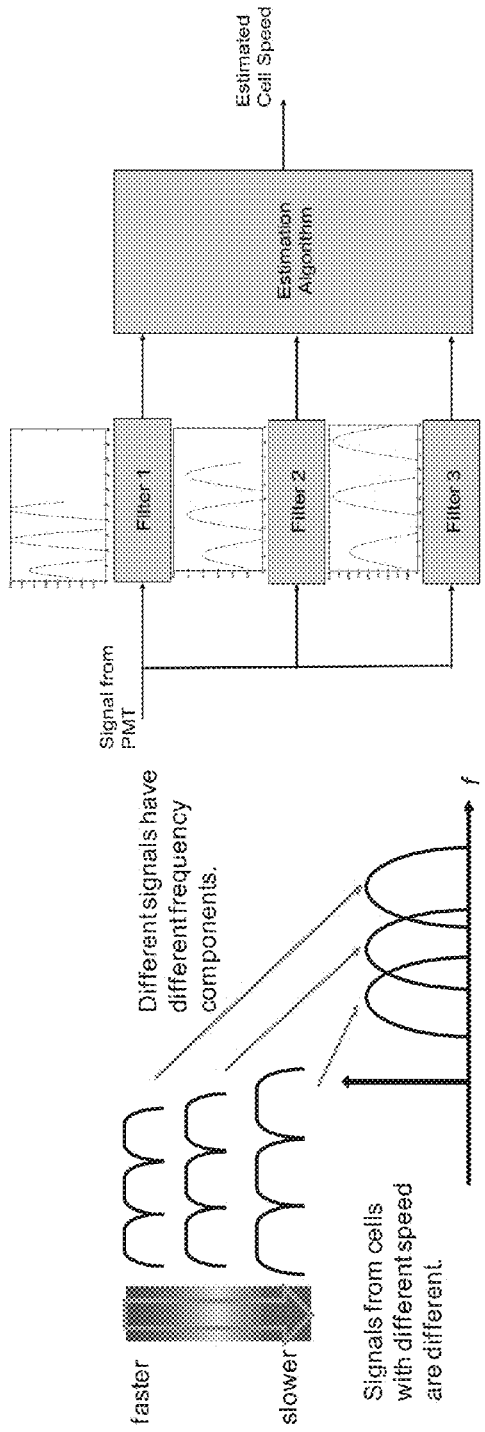
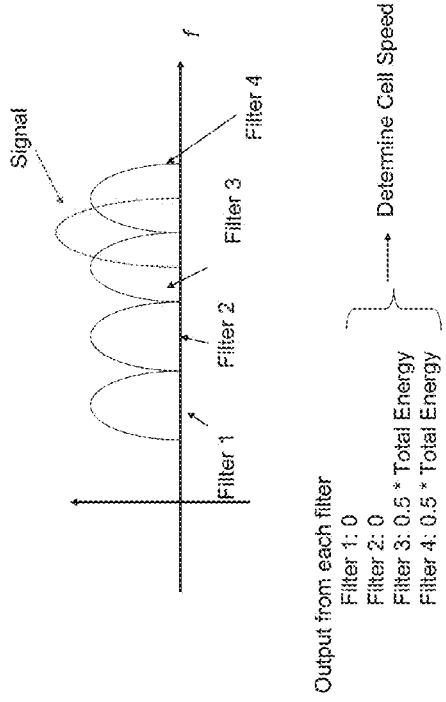
FIG. 12A
FIG. 12B
FIG. 12C

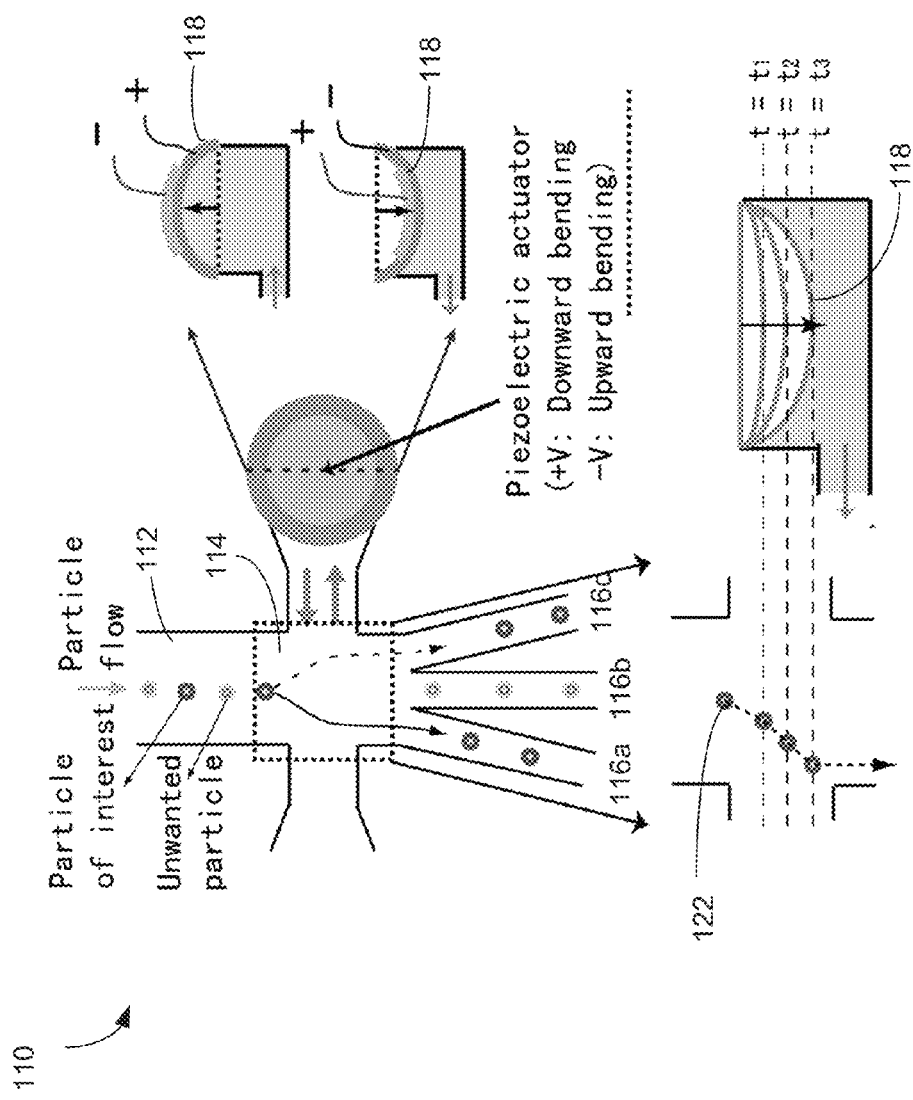

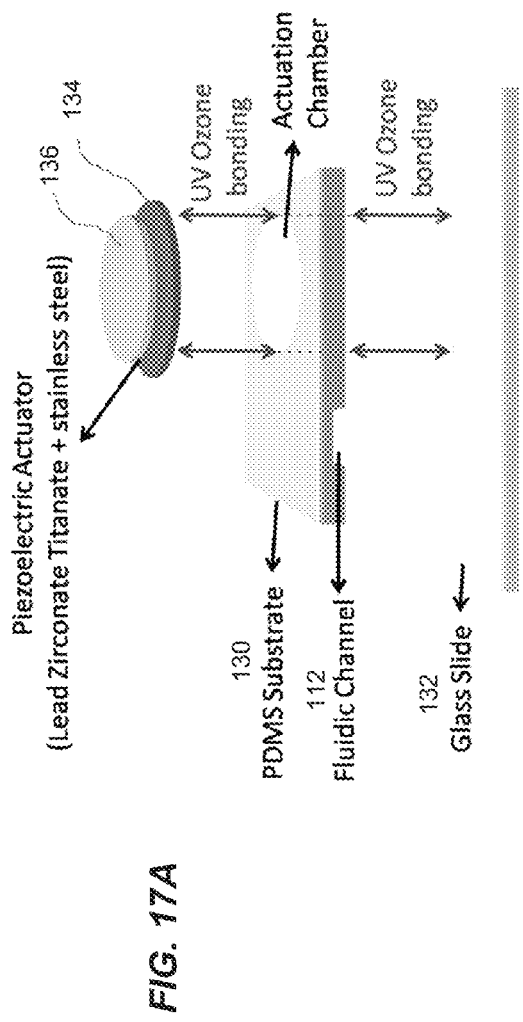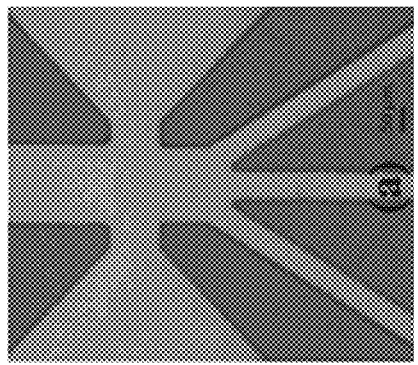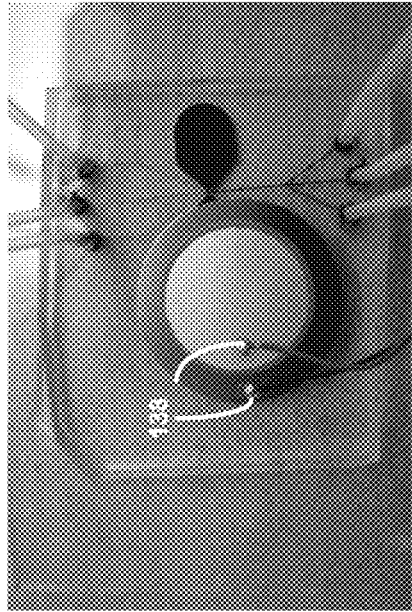
FIG. 17A
FIG. 17B
FIG. 17C

FLUIDIC FLOW CYTOMETRY DEVICES AND PARTICLE SENSING BASED ON SIGNAL-ENCODING

PRIORITY INFORMATION AND RELATED PATENT APPLICATIONS

This patent document is a continuation of U.S. patent application Ser. No. 13/254,851, with a filing date of Nov. 28, 2011, which is a U.S. National Stage application under 35 U.S.C. §371 of International Application No. PCT/US2010/026884, filed on Mar. 10, 2010, which claims priorities of U.S. Provisional Application No. 61/158,969 entitled "Particle sorter and sorting system with piezoelectric actuation" and filed Mar. 10, 2009, and U.S. Provisional Application No. 61/262,787 entitled "Flow cytometry system and method employing color-space-time coding" and filed Nov. 19, 2009, the entire disclosures of which are incorporated by reference as part of the disclosure of this document.

STATEMENT REGARDING FEDERALLY SPONSORED RESEARCH OR DEVELOPMENT

This invention was made with government support under RR024453, RR031424, and RR032225 awarded by the National Institutes of Health. The government has certain rights in the invention.

BACKGROUND

This patent document relates to fluidic devices and techniques in connection with particle sorting in liquid, including cytometry devices and techniques and applications in chemical or biological testing and diagnostic measurements.

Flow cytometry (FC) devices and systems can be used to characterize and analyze particles in liquid, e.g., physical and biochemical properties of cells and biochemical molecules or molecule clusters based on their optical responses as they are interrogated by external light sources in a serial manner. optical signals from such particles can be collected by an optical detector, such as a photomultiplier tube (PMT), and are analyzed or processed to extract information carried by the optical signals on the particles. The optical signals from the particles can be caused by one or more interactions between the input light and the particles such as forward scattering (FSC), side scattering (SSC), and fluorescence.

Cell sorting, including cell sorting at the single-cell level, has become an essential feature in the field of flow cytometry as researchers and clinicians become more interested in studying and purifying certain cells such as stem cells, circulating tumor cells, and rare bacteria species. Cell sorting can be achieved by various techniques. One example is applying vibrations to the jet flow from the nozzle to cause breakage of jet flow into droplets and subsequently using electrically charged plates to deflect cell-containing droplets into their respective collection tubes (droplets of no interest flow straight down to the waste tube without deflection).

Flow cytometry (FC) devices and systems can be implemented based on microfluidic technologies for research assays and diagnostics as well as for clinical applications. Microfluidic technologies range from simple microfluidic channels to complex microfludic devices that can mix fluids, pump liquids, perform digital logic, individually culture cells, determine optimal reaction conditions, and much more. Small-scale fluidic devices have low Reynolds numbers and can be used to achieve controlled laminar flow systems. Microfluidics further offers the advantages of small size for miniaturization and parallelization of devices. The compact size of microfludic devices opens the door to the potential of portable devices. Additionally, various fabrication processes for microfludic devices are suitable for mass production which can reduces the cost of such devices. Advances in microfludic devices can lead to low-cost lab-on-a-chip devices, useful tools to researchers, clinical laboratories, and point-of-care clinicians in remote and/or resource-poor settings.

SUMMARY

This document describes, among others, examples and implementations of techniques and devices for particle sorting in liquid, including cytometry devices and techniques.

In one aspect, a method for providing optical interrogation for flow cytometry includes directing light to one or more of the fluidic channels that are coupled to form a network of fluidic channels to illuminate fluid carried by the fluidic channels; providing optical signal structures that are respectively coupled to at least some of the fluidic channels at different locations to produce optical signals from the light illuminating the fluid, each optical signal carrying information indicative of a property of a particle carried in the fluid at a location of the respective optical signal structure, the optical signal structures being structured to produce, respectively, unique codes in the optical signals that are different from one another; using a single optical detector to collect light from all the optical signals generated at the optical signal structures to produce an electrical detector signal in response to the collected light; and processing the electrical detector signal based on the unique codes in the optical signals to separate information carried by the optical signals to extract information carried by each of the optical signals.

In another aspect, a system for flow cytometry is provided to include an input fluidic channel including a first port for receiving a sample fluid and a second port for outputting the received sample fluid; a particle sorting junction coupled to the second port of the input fluidic channel; branch fluidic channels coupled to the particle sorting junction as outlets of the sample liquid from the second port of the input fluidic channel; an actuator coupled to the particle sorting junction to control a direction of the sample fluid in the particle sorting junction in response to a sorting control signal, the actuator structured to interact with the sample fluid to change the direction of sample fluid to be in different directions corresponding to the branch fluidic channels, respectively, in response to changes in the sorting control signal, wherein the actuator is operable to direct a target particle in the sample fluid into a selected one of the branch fluidic channels; a particle detection module coupled to the input fluidic channel to receive light from the sample fluid in the input fluid channel, the particle detection module including an encoding structure that produces different optical signals from the received light and encodes the different optical signals with different codes; an optical detector that receives the different optical signals to produce a detector signal that carries information of the different optical signals and the different codes; and a particle sorter control module in communication with the particle detection module to receive the detector signal and in communication with the actuator to send the sorting control signal to the actuator, the particle sorter control module including a signal processing mechanism to extract information of the different optical signals from the detector signal based on the different codes in the different optical signals, and a control mechanism that produces the sorting control signal based on the extracted information, including timing of a particle detected at the particle detection module for arriving at the particle sorting junction.

In another aspect, a system for flow cytometry is provided to include an input fluidic channel structured to carry a sample fluid; a particle sorting junction coupled to one end of the input fluidic channel to receive a sample fluid from the input fluidic channel; branch fluidic channels coupled to the particle sorting junction as outlets of the sample liquid from the second port of the input fluidic channel; an actuator coupled to the particle sorting junction to control a direction of the sample fluid in the particle sorting junction in response to a sorting control signal, the actuator structured to interact with the sample fluid to change the direction of sample fluid to be in different directions corresponding to the branch fluidic channels, respectively, in response to changes in the sorting control signal, wherein the actuator is operable to direct a target particle in the sample fluid into a selected one of the branch fluidic channels; a particle detection module coupled to the input fluidic channel to receive light from the sample fluid in the input fluidic channel, the particle detection module structured to produce one or more first optical signals from the received light indicative of at least a speed of a particle in the sample fluid detected by the particle detection module; a branch verification structure coupled to one of the branch fluidic channels to receive light from the one branch fluidic channel and to produce a branch verification optical signal that can be used to verify whether a target particle is directed by the actuator into the one branch fluidic channel; an optical detector located to receive light which includes at least the one or more first optical signals from the particle detection module and the branch verification optical signal and to produce a detector signal that carries information contained in the received light; and a particle sorter control module in communication with the particle detection module to receive the detector signal and in communication with the actuator to send the sorting control signal to the actuator, the particle sorter control module including a signal processing mechanism to extract information from the detector signal, including timing of a particle detected at the particle detection module for arriving at the particle sorting junction based on information on the speed of the particle carried by the detector signal, and a control mechanism that produces the sorting control signal based on the extracted information, including the timing of the particle for arriving at the particle sorting junction. The signal processing mechanism in the particle sorter control module extracts information of the branch verification optical signal to produce an indicator that verifies whether a target particle is directed by the actuator into the one branch fluidic channel.

In another aspect, a system for flow cytometry is provided to include an input fluidic channel structured to carry a sample fluid; a particle sorting junction coupled to one end of the input fluidic channel to receive a sample fluid from the input fluidic channel; branch fluidic channels coupled to the particle sorting junction as outlets of the sample liquid from the second port of the input fluidic channel; an actuator coupled to the particle sorting junction to control a direction of the sample fluid in the particle sorting junction in response to a sorting control signal, the actuator structured to interact with the sample fluid to change the direction of sample fluid to be in different directions corresponding to the branch fluidic channels, respectively, in response to changes in the sorting control signal, wherein the actuator is operable to direct a target particle in the sample fluid into a selected one of the branch fluidic channels; a particle detection module coupled to the input fluidic channel to receive light from the sample fluid in the input fluidic channel, the particle detection module structured to produce one or more first optical signals from the received light indicative of at least a speed of a particle in the sample fluid detected by the particle detection module, each first optical signal being encoded with a unique first code; a branch optical signal structure coupled to one of the branch fluidic channels to receive light from the one branch fluidic channel and to produce a second optical signal that indicates a property of a particle in the one branch fluidic channel and is encoded with a unique second code that is different from each first code; an optical detector located to receive light which includes at least the one or more first optical signals from the particle detection module and the second optical signal and to produce a detector signal that carries information contained in the received light; and a particle sorter control module in communication with the particle detection module to receive the detector signal and in communication with the actuator to send the sorting control signal to the actuator, the particle sorter control module including a signal processing mechanism to extract information from the detector signal, including timing of a particle detected at the particle detection module for arriving at the particle sorting junction based on information on the speed of the particle carried by the detector signal, and a control mechanism that produces the sorting control signal based on the extracted information, including the timing of the particle for arriving at the particle sorting junction. The signal processing mechanism of the particle sorter control module separates information carried by the one or more first optical signals and the second optical signal based on the first codes and the second code.

In another aspect, a system for flow cytometry is provided to include fluidic channels structured to carry fluid and to form a network of fluidic channels; a light coupling structure to couple light into one or more of the fluidic channels to illuminate the fluid therein; optical signal structures that are respectively coupled to at least some of the fluidic channels at different locations to produce optical signals from the light illuminating the fluid, each optical signal carrying information indicative of a property of a particle carried in the fluid at a location of the respective optical signal structure, optical signal structures being structured to produce, respectively, unique codes in the optical signals that are different from one another; an optical detector that is positioned to receive the optical signals from the optical signal structures and to produce a detector signal based on received light of the optical signals; and a processing circuit coupled to the optical detector to receive the detector signal, the processing circuit separating information carried by the optical signals based on the unique codes to extract information carried by each of the optical signals.

In another aspect, a particle sorter for sorting particles in a fluid is provided to include a structure having an input channel connected at an actuation area to a plurality of output channels, wherein the particles in the fluid flow through the input channel to the actuation area, and each particle travels from the actuation area to one of the plurality of output channels, and a piezoelectric actuator for causing a flow disturbance in the actuation area in response to a control signal, wherein the flow disturbance operates to direct a particle along a trajectory to one of the plurality of output channels which is different than the output channel to which the particle would travel without the flow disturbance.

In another aspect, a particle sorting system for sorting particles of interest from other particles in a fluid is provided to include a structure having at least one input channel connected at an actuation area to a plurality of output channels, wherein the fluid flows through the input channel to the actuation area, and each particle travels from the actuation area to one of the plurality of output channels, a spatial filter having one or more slots and coupled to the input channel, a detector for generating a detection signal over time indicative of light emitted or scattered from a particle of interest, which light has passed through the one or more slots of the spatial filter, a processor in communication with the detector for analyzing the detection signal over time and generating a presence signal indicative of the presence of a particle of interest, a driver in communication with the processor and generating a control signal in response to the presence signal, and a piezoelectric actuator for causing a flow disturbance in the actuation area in response to the control signal, wherein the flow disturbance operates to direct a detected particle of interest along a trajectory to one of the plurality of output channels which is different than the output channel to which the particle would travel without the flow disturbance.

In another aspect, a particle sorting system for sorting particles of interest from other particles in a fluid includes a structure having at least one input channel connected at an actuation area to a plurality of output channels, wherein the fluid flows through the input channel to the actuation area, and each particle travels from the actuation area to one of the plurality of output channels, a spatial filter having one or more slots and coupled to the input channel, a detection unit that detects a particle of interest at a predetermined location and generating a control signal in response, and a piezoelectric actuator for causing a flow disturbance in the actuation area in response to the control signal. The flow disturbance operates to direct a detected particle of interest along a trajectory to one of the plurality of output channels which is different than the output channel to which the particle would travel without the flow disturbance.

In another aspect, a system for flow cytometry is provided to include a microfluidic channel; a first light conveying structure configured to convey substantially all visible light components, and having a first end proximate the microfluidic channel; at least one second light conveying structure having at least one second end proximate the microfluidic channel, and extending substantially alongside the first light conveying structure, wherein the at least one second light conveying structure is configured to convey at least one subset of the visible light components; and a light sensing device arranged proximate respective additional ends of each of the light conveying structures, the respective additional ends being respectively opposite the respective first and second ends. Respective portions of light emanating from material passing through the microfluidic channel are received by the respective light conveying structures and communicated at least in part thereby to the light sensing device. An indication of the material passing through the microfluidic channel can be determined based upon one or more signals output by the light sensing device.

In another aspect, a method of performing flow cytometry is provided to include injecting first light into a microfluidic channel through which material is passing; receiving second light from the microfluidic channel into a plurality of waveguides, wherein a first of the waveguides is conductive of substantially all visible light components, and a second of the waveguides is conductive of a subset of the visible light components; and conveying first and second portions of the second light through the first and second waveguides from respective first ends of the waveguides to respective second ends of the waveguides; and communicating at least some of each of the conveyed first and second portions of the second light to a photodetector; and outputting a color-space-time signal from the photodetector.

In yet another aspect, a method of performing flow cytometry is provided to include injecting first light into a microfluidic channel through which material is passing; receiving second light from the microfluidic channel into a plurality of optical filters, wherein a first of the filters is conductive of substantially all visible light components, and a second of the filters is conductive of a subset of the visible light components; communicating at least some of each of the conveyed first and second portions of the second light to a photodetector; and outputting a color-space-time signal from the photodetector.

These and other aspects and implementations are described in detail in the drawings, the detailed description and the claims.

BRIEF DESCRIPTION OF THE DRAWINGS

FIG. 7A is a further schematic view of portions of the FACS device of FIG. 6A, which further shows matter of interest (in this embodiment, cells) passing through a microfluidic channel of the FACS device.

FIGS. 7B and 7C are respective cross-sectional views of the FACS device of FIGS. 2-4A, taken along lines B-B and C-C of FIG. 7A.

FIGS. 12A, 12B and 12C show signal processing via a bank of filters at different signal frequencies in determining the cell speed. FIG. 12A shows Cells with different speeds generate different signals in time and frequency domains. FIG. 12B shows that Filter-bank architecture can be applied to estimate the speed of each individual cell by matching its signal waveform to different filters in the filter-bank. FIG. 12C shows a processing example.

FIG. 15 illustrates a particle sorter and its operation in accordance with at least one embodiment of the present invention;

FIGS. 17A, 17B and 17C illustrate the fabrication of a particle sorter of FIG. 15;

DETAILED DESCRIPTION

Examples of devices, systems and techniques for flow cytometry described in this document implement various technical features that are either alone or in various combinations can be used to achieve one or more technical benefits. One of the technical features, for example, is to provide optical illumination to the fluid in a flow cytometer device or system to allow optical sensing or monitoring in performing flow cytometry operations. The functionality of microfluidics can be combined with photonics to create a technology platform that provides integrated microfluidic photonics. Embracing photonics is a logical path of evolution for microfluidics, as a wide range of techniques for biological and chemical detection are photonic in nature. Fluorescence, fluorescence resonance energy transfer (FRET), optical scattering, and surface-enhanced Raman spectroscopy (SERS) are examples of effective and accurate methods to detect analytes at the cellular and molecular level. Integration of microfluidics with photonics represents not only a new technology platform but also a transformation to the new paradigm of bio-system-on-a-chip (BSoC). Integrated microfluidic photonic circuits have promising applications in biomedicine.

A flow cytometer based on FACS (fluorescence-activated cell sorter) is one example for combining photonics and microfluidics to meet some of the aforementioned requirements and can be a valuable bioanalysis tool for characterizing physical and biochemical properties of various chemical or biological particles, e.g., molecule clusters and cells, in a highly quantitative manner, and for detecting and monitoring the progression of diseases such as acute myeloid leukemia (AML) and AIDS. With the addition of the cell sorting capability to enrich the purity of biospecimens and extract rare cell types, a FACS can interrogate and sort cells with a throughput of tens of thousands of cells per second, making possible rare-event studies such as identification of bacterial cells or isolation of stem cells or tumor cells.

Various technical features described herein can be used to form a flow cytometer based on FACS. With the advent of lab-on-a-chip technologies, bulk optics in a FACS can now be replaced with integrated optics, affording some level of device miniaturization and cost reduction. The availability of small and inexpensive diode lasers—originally developed for optical disk and other devices—has also provided impetus for the development of micro FACS. Multicolor detection that scales with a lab-on-a-chip platform can be achieved in an integrated system described in this document by eliminating multiple photodetectors such as PMTs and by providing signal encoding in different optical signals generated in the system.

Figure 1:
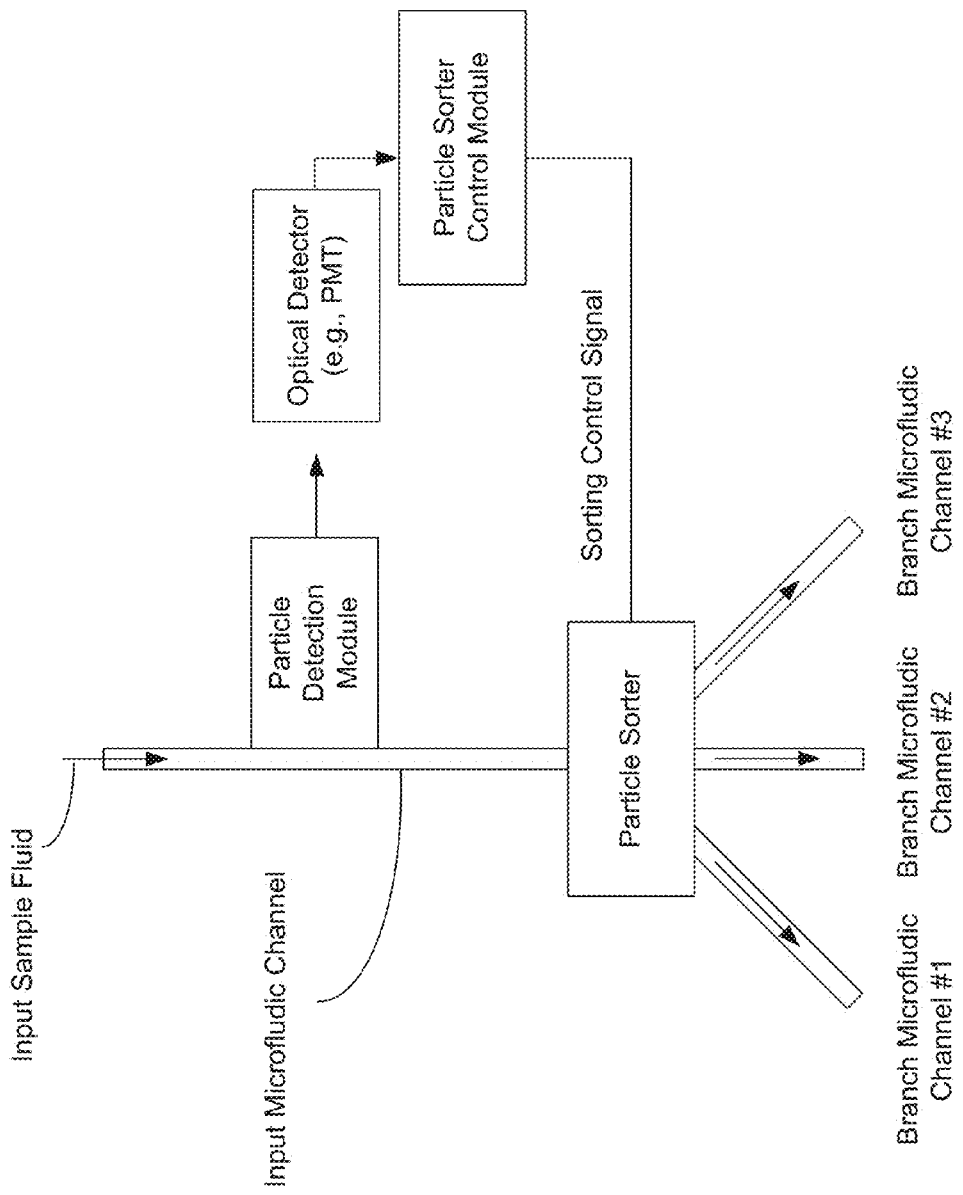
FIGS. 1, 2, 3A, 3B and 3C show examples of flow cytometry systems.

FIG. 1 shows an example of a system for flow cytometry in which various technical features described in this document can be implemented. This system includes an input fluidic channel including a first port for receiving a sample fluid or the input sample fluid, and a second port for outputting the received sample fluid. A particle sorting junction or a particle sorter is provided for sorting particles within the sample fluid and is coupled to the second port of the input fluidic channel. Downstream from the particle sorting junction, two or more branch fluidic channels are coupled to the particle sorting junction as outlets of the sample liquid from the second port of the input fluidic channel. An actuator is coupled to the particle sorting junction to control a direction of the sample fluid in the particle sorting junction in response to a sorting control signal. This actuator can reside inside the particle sorting junction or in a fluid containing region that is adjacent to or in fluid communication with the particle sorting junction so that the movement of the actuator causes movement of the sample fluid at the particle sorting junction to change the flow direction of the sample fluid. In this regard, the actuator is structured to interact with the sample fluid to change the direction of sample fluid to be in different directions corresponding to the branch fluidic channels, respectively, in response to changes in the sorting control signal. Under this design, the actuator is operable to direct a target particle in the sample fluid into a selected one of the branch fluidic channels.

The actuator for sorting particles in FIG. 1 can be implemented based on various cell sorting techniques. Examples of sorting techniques include electric field-based sorting, dielectrophoretic (DEP) sorting, magnetic sorting, and hydrodynamic sorting. Sorting is useful for the detection and isolation of rare stem cells, circulating tumor cells, and E. coli cells, among others. Implementing a hydrodynamic sorter may involve external check values, integrated valves, or external syringe pumps. Notably, the actuator in FIG. 1 can be implemented to include a piezoelectric actuator that moves in response to a voltage signal as the sorting control signal to cause the sample fluid in the particle sorting junction to change the flow direction. Such a microfluidic cell sorter with integrated piezoelectric actuator is easy to fabricate and can operate at low voltages, e.g., less than 10 Vp-p. In the experiment of instantaneous flow switching, a prototype piezoelectrical actuator can be operated to change the flow stream at a relatively high frequency (e.g., ~1.7 kHz) and the amount of deflection of cells/particles in the flow can be precisely controlled. Particles of varying size, shape, and density of interest can be individually sorted in a controlled manner by the present piezoelectrical actuator. In the experiment of E. *Coli* deflection, a sinusoidal voltage deflects cells at a rate of 330 cells/s and shows a highly repeatable operation in consistent with the theory. Using a specially design spatial filter and a real-time signal processing algorithm implemented in FPGA, a closed-loop sorting system can be built with a low error rate and a sorting efficiency of around 70%. Compared with other µFACS, our sorting system has a number of advantages. For example, the spatial filter design and the real-time signal processing algorithm enhance the signal-to-noise ratio by 18 dB and allow verification of sorting. For another example, the PZT-actuated sorting module is easy to fabricate, consumes little power (e.g., 0.1 mW), operates at a low voltage (e.g., <10 Vpp), and has a much faster response (e.g., 0.1-1 ms) than off-chip mechanical actuators such as check-valves and syringe pumps. As yet another example, the FPGA-based electronics control enables real-time signal amplification, user-defined delay time, programmable output waveform, and low timing jitter (e.g., <10 µsec). These features contribute significantly to a low-cost sorter that can perform high-throughput cell sorting at a single-cell level.

In the system in FIG. 1, a particle detection module is coupled to the input fluidic channel to receive light from the sample fluid in the input fluid channel. The light can be obtained form a light source such as a laser or other light source and the light is directed to illuminate the sample fluid in the input fluidic channel. This illumination of a particle in the sample fluid causes light to be generated by the particle. As such, the particle detection module produces one or more first optical signals from the received light indicative of at least a speed of a particle in the sample fluid detected by the particle detection module. In some implementations, the particle detection module can include an encoding structure that produces different optical signals from the received light and encodes the different optical signals with different codes. This encoding can be spaced-based codes or time-based codes and allows for using a single optical detector to detect multiple optical signals in the system, e.g., different optical signals from different locations in the system. An optical detector such as a PMT or avalanche photodiode is provided to receive the one or more optical signals from the particle detection module or light from other locations in the system to produce a detector signal that carries information carried by the received light. The information in the received light is extracted out by processing the detector signal from the optical detector for various purposes, including controlling the actuator and the respective sorting in the particle sorting junction.

In FIG. 1, a particle sorter control module is provided to be in communication with the particle detection module to receive the detector signal and in communication with the actuator to send the sorting control signal to the actuator. The particle sorter control module includes a signal processing mechanism to extract information from the detector signal by processing the detector signal with proper processing techniques, e.g., by using a digital signal processing (DSP) circuitry. When the optical signals are encoded, the signal processing mechanism can process the detector signal based on the different codes in the different optical signals to separate information carried by different optical signals. The particle sorter control module also includes a control mechanism that produces the sorting control signal based on the extracted information, including timing of a particle detected at the particle detection module for arriving at the particle sorting junction.

In the specific example in FIG. 1, different branch microfluidic channels #1, #2 and #3 are coupled to the particle sorting junction to receive the sorted particles from the particle sorting junction.

Figure 2:
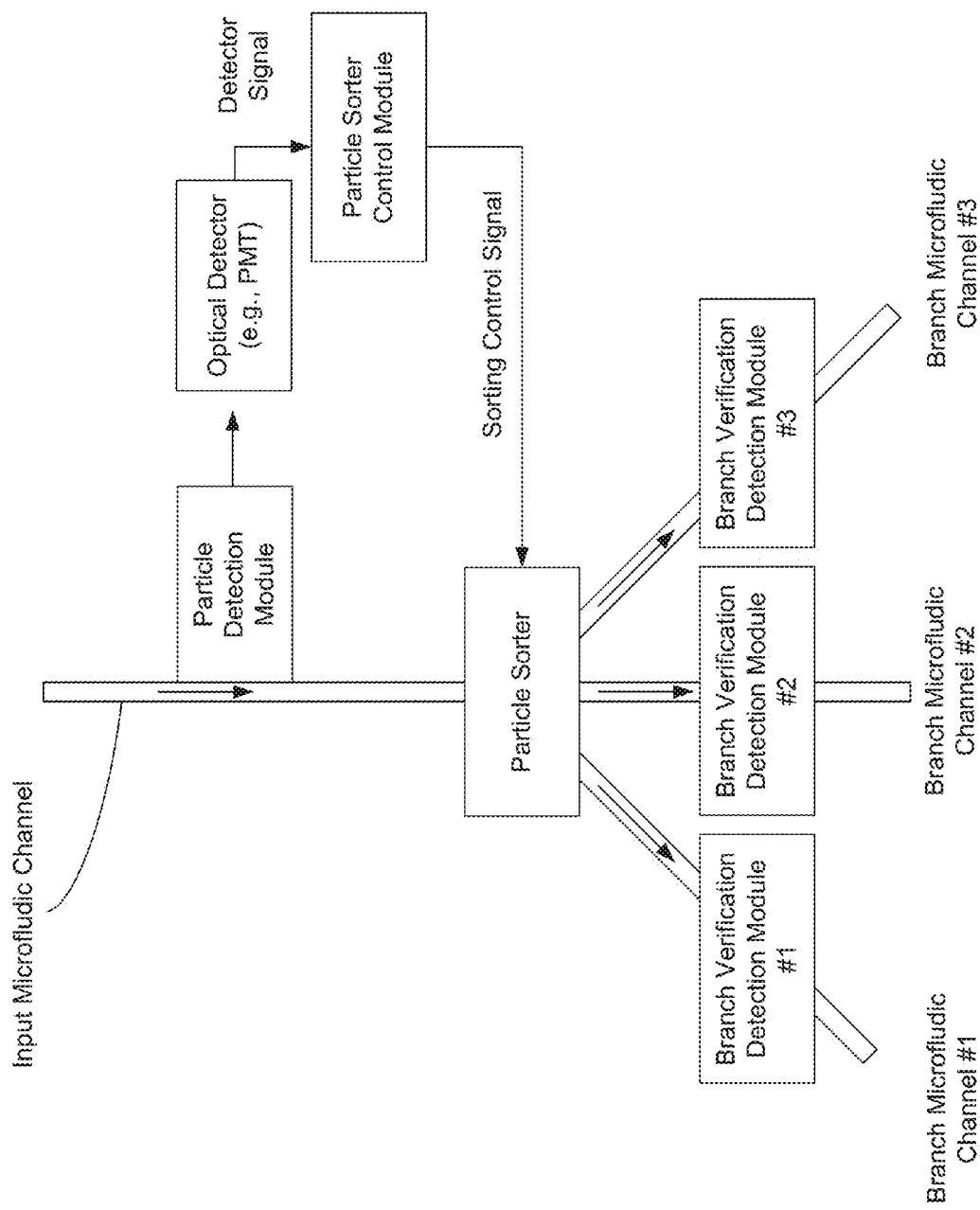

FIG. 2 shows another exemplary system for flow cytometry which provides an optical sensing mechanism in one or more branch fluidic channels downstream from the particle sorting junction. This combination of using the optical sensing at a pre-sorting location and optical sensing at a post-sorting location in the system can be used to provide better controlled operation for more efficient flow cytometry measurements. In the illustrated example, the post-sorting sensing is used to verify whether a desired particle sorting performed by the actuator in the particle sorting junction is properly executed.

The system in FIG. 2 has similar features in the system in FIG. 1. Different from FIG. 1, the system in FIG. 2 includes a branch verification structure that is coupled to one of the branch fluidic channels to receive light from the one branch fluidic channel and to produce a branch verification optical signal that can be used to verify whether a target particle is directed by the actuator into the one branch fluidic channel. Two or more such branch verification structures can be implemented in some systems. In FIG. 3, all three branch fluidic channels have such verification detection modules. In some systems, only selected branches may have such verification structures while some branches may not.

In FIG. 2, the optical detector is located to receive light which includes at least the one or more optical signals from the particle detection module and the branch verification optical signal. The optical detector produces a detector signal that carries information contained in the received light. The signal processing mechanism in the particle sorter control module extracts information of the branch verification optical signal to produce an indicator that verifies whether a target particle is directed by the actuator into the one branch fluidic channel. In some systems, this verification may be automatically fed back to the particle sorter control module which may, in response to a verification of malfunction in the sorting, interrupt the system operation, e.g., stopping the incoming sample flow and the sorting operation by the actuator. In other systems, an alert signal may be generated by the particle sorter control module to alert the operator of the system of this malfunction in the sorting.

One of technical limitations in some other flow cytometry systems is using multiple PMTs to respectively detect optical signals at different fluorescent wavelengths. Presence of multiple PMTs in such systems complicates the system design, increases the cost, and renders the systems bulky and heavy. One of technical features described in this document is to provide signal encoding in multiple different optical signals so that different optical signals are encoded with unique and mutually different or orthogonal codes. As such, these optical signals can be multiplexed together for optical detection by a single optical detector and the information carried by the different optical signals can be separated by demultiplexing based on the unique and mutually different or orthogonal codes. The demultiplexing can be performed via digital signal processing.

Figure 3A:
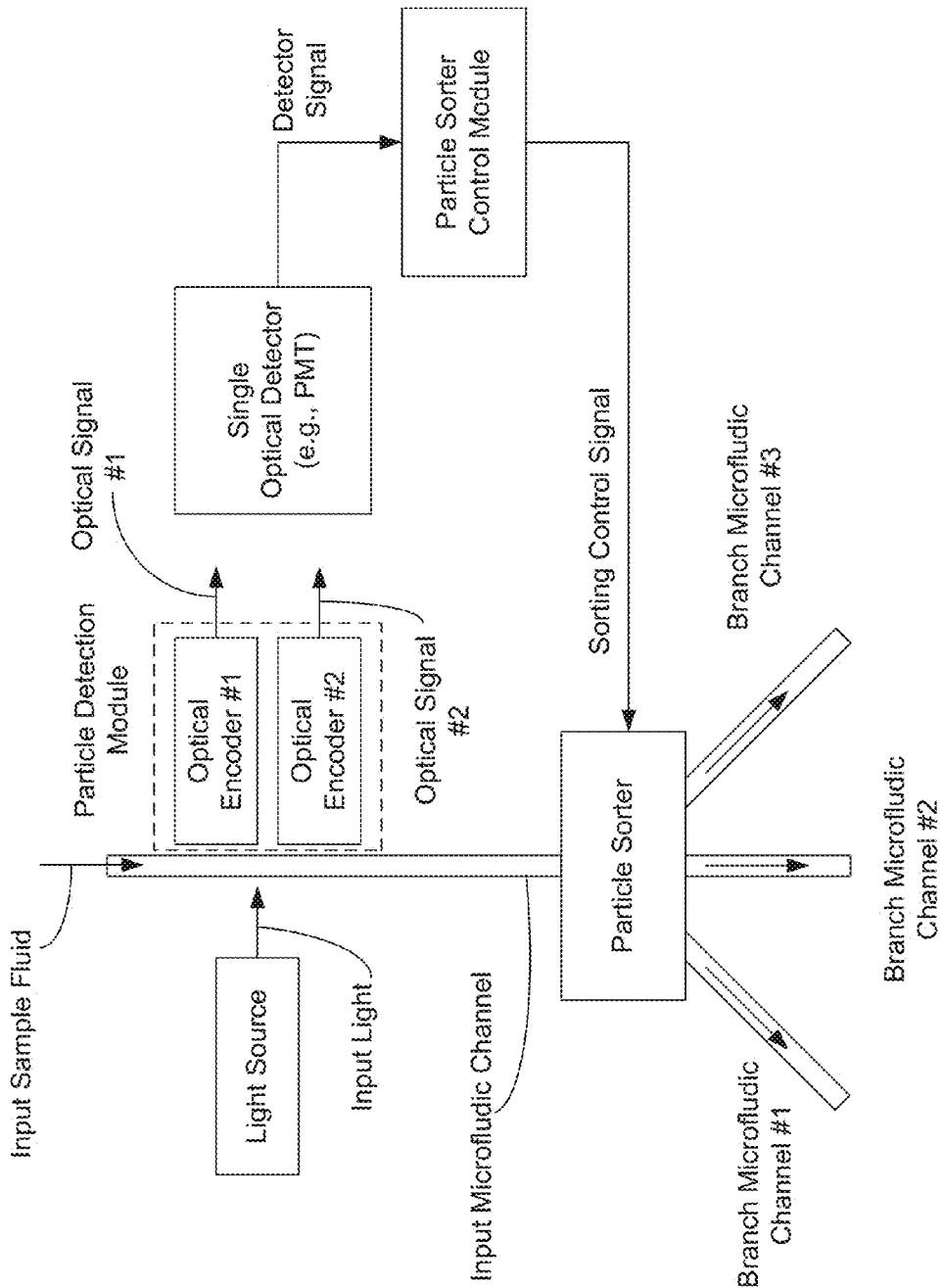
Figure 3B:
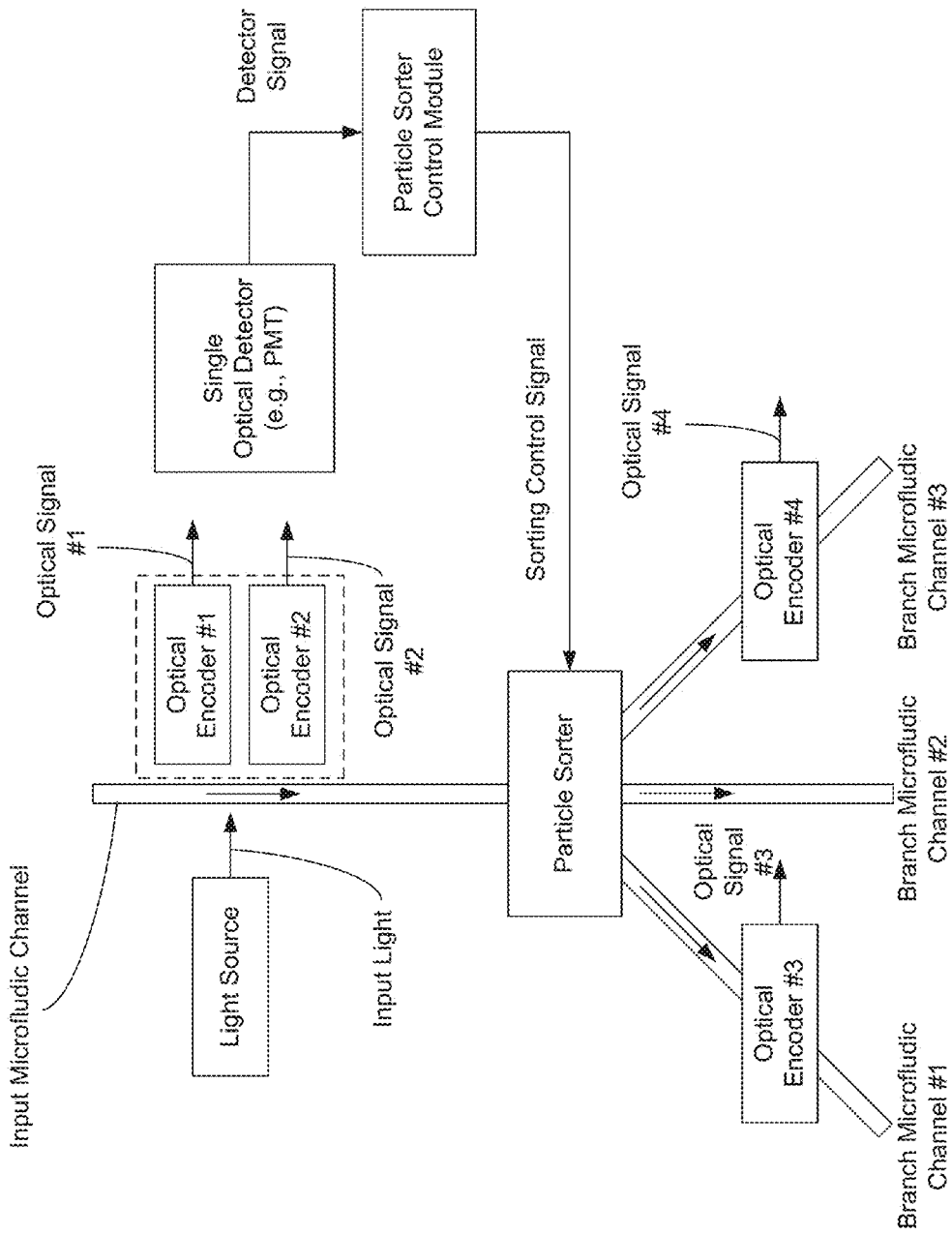

FIGS. 3A and 3B show two system examples that implement such signal encoding.

In FIG. 3A, the particle detection module coupled to the input fluidic channel is structured to include an encoding structure that produces different optical signals from the received light and encodes the different optical signals with different codes. Two optical encoders #1 and #2 are shown as examples of such an encoding structure. The first optical encoder #1 produces a first optical signal with a first code and the second optical encoder #2 produces a second optical signal with a second code that is different from the first code. The optical detector receives the different optical signals to produce a detector signal that carries information of the different optical signals and the different codes. The signal processing mechanism, e.g., the DSP, of the particle sorter control module extracts information of the different optical signals from the detector signal based on the different codes in the different optical signals. The control mechanism in the particle sorter control module produces the sorting control signal based on the extracted information, including timing of a particle detected at the particle detection module for arriving at the particle sorting junction.

In FIG. 3B, additional optical encoders are provided in the system to allow for the same optical detector to detect the encoded optical signals. The two additional optical encoders #3 and #4 are shown as examples of encoding structures in the branch fluidic channels #1 and #3, respectively. The third optical encoder #3 produces a third optical signal #3 with a third code different from the first and second codes and the fourth optical encoder #4 produces a fourth optical signal with a fourth code that is different from all other three codes. The optical detector receives the different optical signals #1-#4 to produce a detector signal that carries information of the different optical signals #1-#4 and the different codes. As a specific example, referring to FIG. 2, the third and fourth optical signals in FIG. 3B can be the branch verification optical signals when each of the optical encoders #3 and #4 are implemented as branch verification structures. The optical detector receives both the two optical signals #1 and #2 and the branch verification optical signals #3 and #4.

Figure 3C:
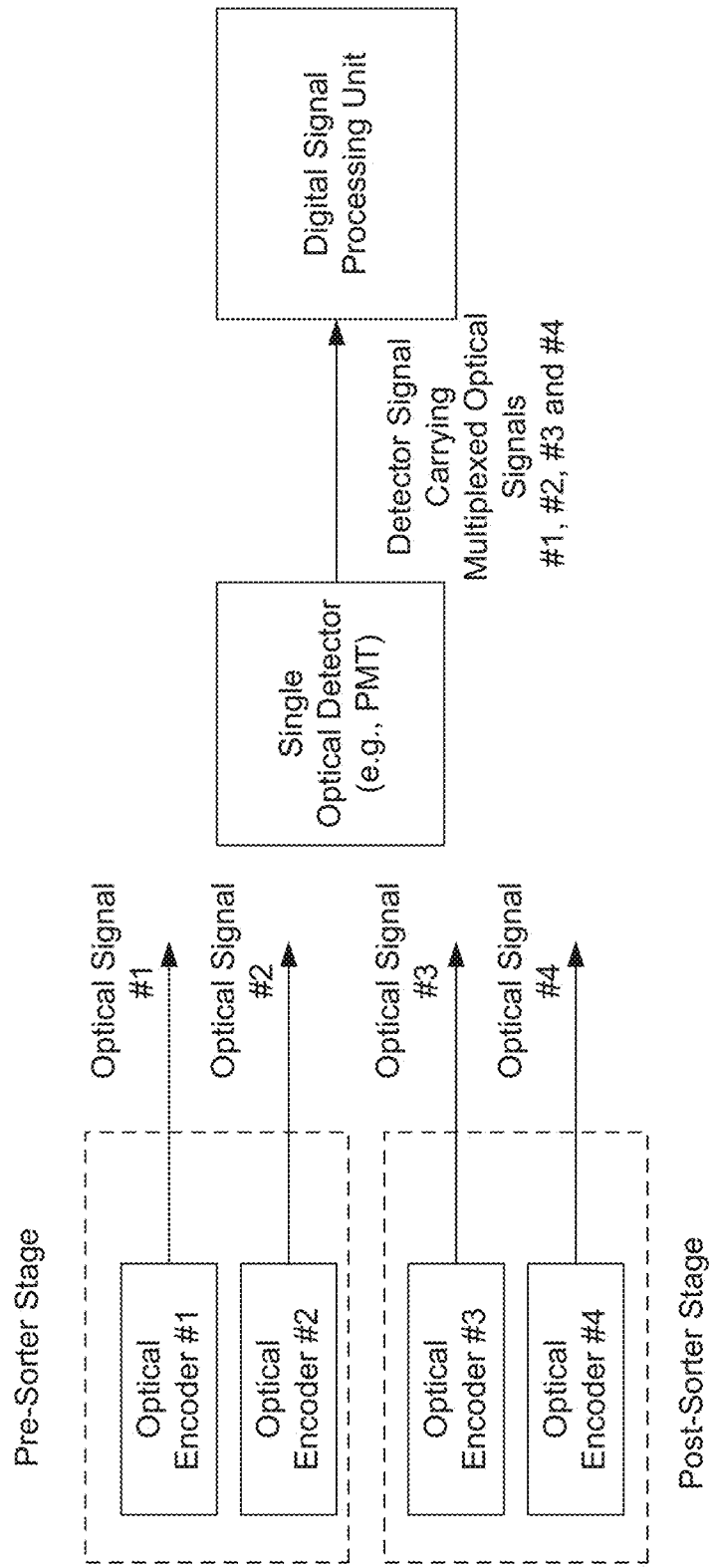

FIG. 3C shows the signal detection and processing in FIG. 3B. The signal detection is performed by the single optical detector that receives light of all four optical signals #1-#4 which are multiplexed together as the input light which is converted into the detector signal carrying the multiplexed signals #1-#4. After a analog to digital conversion, a DSP unit is used to process the multiplexed signal and to separate the four different signals based on their unique codes.

Hence, the above examples for optical encoding and decoding in flow cytometry are based on an optical interrogation method with a single optical detector based on signal encoding via optical signal structures like optical encoders illustrated in FIGS. 3A-3C. This method includes directing light to one or more of the fluidic channels that are coupled to form a network of fluidic channels to illuminate fluid carried by the fluidic channels and providing optical signal structures that are respectively coupled to at least some of the fluidic channels at different locations to produce optical signals from the light illuminating the fluid. Each optical signal carries information indicative of a property of a particle carried in the fluid at a location of the respective optical signal structure. The optical signal structures are structured to produce, respectively, unique codes in the optical signals that are different from one another. This method uses a single optical detector to collect light from all the optical signals generated at the optical signal structures to produce an electrical detector signal in response to the collected light. The electrical detector signal is processed based on the unique codes in the optical signals to separate information carried by the optical signals to extract information carried by each of the optical signals.

Specific examples of signal encoding and decoding based on a COlor-Space-Time (COST) encoding are described below in which an improved flow cytometry system can be achieved by COST to support detection of multiple (e.g., 20 or more) fluorescent wavelengths using a single detector and, more particularly in at least some embodiments, a single photo-multiplier tube (PMT) or single-photon avalanche detector (SPAD) or avalanche photodiode. In at least some embodiments, the improved flow cytometry system is implemented using lab-on-a-chip technology and architecture. A simpler version of such architecture (which can be referred to as space-time coding) in at least some embodiments is also provided to allow for multi-point detection and the consequent generation of "verification signals" to record sorting efficiency and accuracy in real time.

The following examples include methods and architectures, and/or devices embodying such, for COST coded detection of multiple fluorescent wavelengths using a single detector within a lab-on-a-chip fluorescence-activated cell sorter (FACS) or flow cytometer. Such embodiments can be considered an extension of space-time coding, which is modified to include color coding by incorporating color dyes in the waveguides transmitting the fluorescence to the detector. With the appropriate choice of dyes and calibration of the absorption spectrum, twenty or more fluorescent wavelengths can pass through the color-filter waveguides and be detected using a single detector such as a PMT or SPAD. Although in some embodiments of the present invention, colored waveguides/filters are integrated on a chip to achieve COST coded detection, in other embodiments it is also possible to implement the COST concept using one or more external color filters not integrated with the chip. In such case, when the chip is disposed of after a single use or a few uses, the color filter(s) is/are not (or need not be) disposed of.

In at least some additional embodiments, the flow cytometer and/or FACS also include one or more additional components and/or features. These can include, for example, an array of integrated lenses that focus light and shorten the interrogation zone to enhance detection throughput. Also, these features can include flow disturbance minimization, 3D flow confinement and/or cascaded sorting strategies to achieve >1M enrichment factor with minimum cell loss. Also, these features can include system integration architectures with real-time electronic control and signal processing algorithms to coordinate detection and sorting, enhance sensitivity and minimize sorting error. In at least some embodiments, the COST approach provides an integrated, optofluidic solution to multicolor detection thus enabling the construction of FACS or flow cytometers that are orders of magnitude smaller, lighter and/or less expensive than existing commercial systems.

In at least one embodiment, a system for flow cytometry includes a microfluidic channel, and a first light conveying structure configured to convey substantially all visible light components, and having a first end proximate the microfluidic channel. The system also includes at least one second light conveying structure having at least one second end proximate the microfluidic channel, and extending substantially alongside the first light conveying structure, where the at least one second light conveying structure is configured to convey at least one subset of the visible light components. The system further includes a light sensing device arranged proximate respective additional ends of each of the light conveying structures, the respective additional ends being respectively opposite the respective first and second ends. Respective portions of light emanating from material passing through the microfluidic channel are received by the respective light conveying structures and communicated at least in part thereby to the light sensing device, whereby an indication of the material passing through the microfluidic channel can be determined based upon one or more signals output by the light sensing device.

Additionally, in at least one embodiment, a method of performing flow cytometry includes injecting first light into a microfluidic channel through which material is passing, and receiving second light from the microfluidic channel into a plurality of waveguides, where a first of the waveguides is conductive of substantially all visible light components, and a second of the waveguides is conductive of a subset of the visible light components. The method further includes conveying first and second portions of the second light through the first and second waveguides from respective first ends of the waveguides to respective second ends of the waveguides, communicating at least some of each of the conveyed first and second portions of the second light to a photodetector, and outputting a color-space-time signal from the photodetector.

Further, in at least one embodiment, a method of performing flow cytometry includes injecting first light into a microfluidic channel through which material is passing, and receiving second light from the microfluidic channel into a plurality of optical filters, where a first of the filters is conductive of substantially all visible light components, and a second of the filters is conductive of a subset of the visible light components. The method additionally includes communicating at least some of each of the conveyed first and second portions of the second light to a photodetector; and outputting a color-space-time signal from the photodetector.

Figure 4:
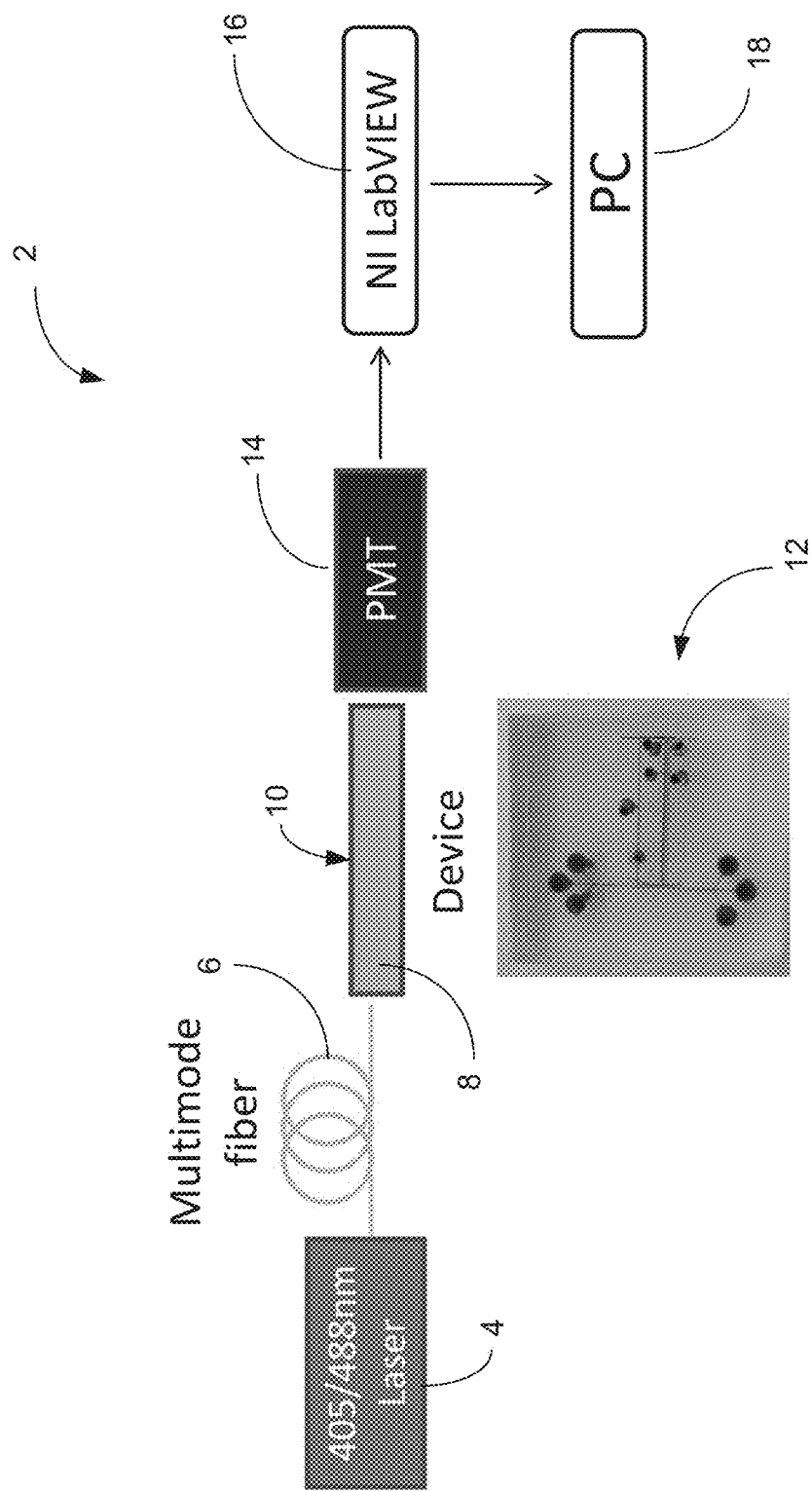
FIG. 4 is a schematic diagram showing components of an exemplary fluorescence-activated-cell-sorter (FACS) system.

Referring to FIG. 4, a schematic view is provided of an exemplary fluorescence-activated-cell-sorter (FACS) system 2 in accordance with one embodiment of the present invention. As shown, the FACS system 2 includes a laser 4 that generates laser light and provides that light into a multimode fiber 6. The multimode fiber 6 in turn directs the light toward a FACS device 10 represented schematically by a box 8. An image 12 of internal components of the FACS device 10 is also provided adjacent to the box, and those internal components are described in further detail below. Finally, after the light has been provided to the FACS device 10, the light interacts with the cells or other materials or matter passing through a microfluidic channel (described further below) of that device and, as a result of that interaction, resultant light is provided from the FACS device 10 to a photo-multiplier tube (PMT) 14 that senses that light. The PMT 14 upon sensing of the light in turn output signals indicative of the sensed light to National Instruments LabView-based software 16 (available from National Instruments Corp. of Austin, Tex.), which in turn provides data to personal computer 18 (notwithstanding the representation provided in FIG. 1, the software 16 can be considered implemented on the personal computer).

In the embodiment in FIG. 4 and at least some other embodiments, multiple parameter detection is achieved by applying COlor-Space-Time (COST) coding technology. Multiple parameter detection is of greater interest when it allows for detection of 12 or more different fluorescent wavelengths of light emanating from the FACS device 10. In the embodiment of FIG. 4, it is envisioned that the FACS system 2 can support detection of multiple (e.g., 20 or more) fluorescent wavelengths of light emanating from the FACS device 10 using a single detector. The single detector can take different forms depending upon the embodiment and, while FIG. 4 shows the PMT 14 as the single detector, in other embodiments, the detector can take other forms, for example, a single-photon avalanche detector (SPAD).

The laser light source 4 in the present embodiment takes the form of a 405/488 nm (or Blu-ray standard) laser. In other embodiments, a variety of other excitation lasers can be used instead (e.g, lasers at 630-650 nm and/or other lasers manufactured by a variety of companies such as Nichia, Sony, Xerox, Omicron, etc.). Additionally, in the embodiment of FIG. 4, and at least some other embodiments, the FACS system 2 or at least certain portions thereof (e.g., the FACS device 10) can be devices employing a lab-on-a-chip technology platform that replaces the bulk optics with integrated optics.

Figure 5:
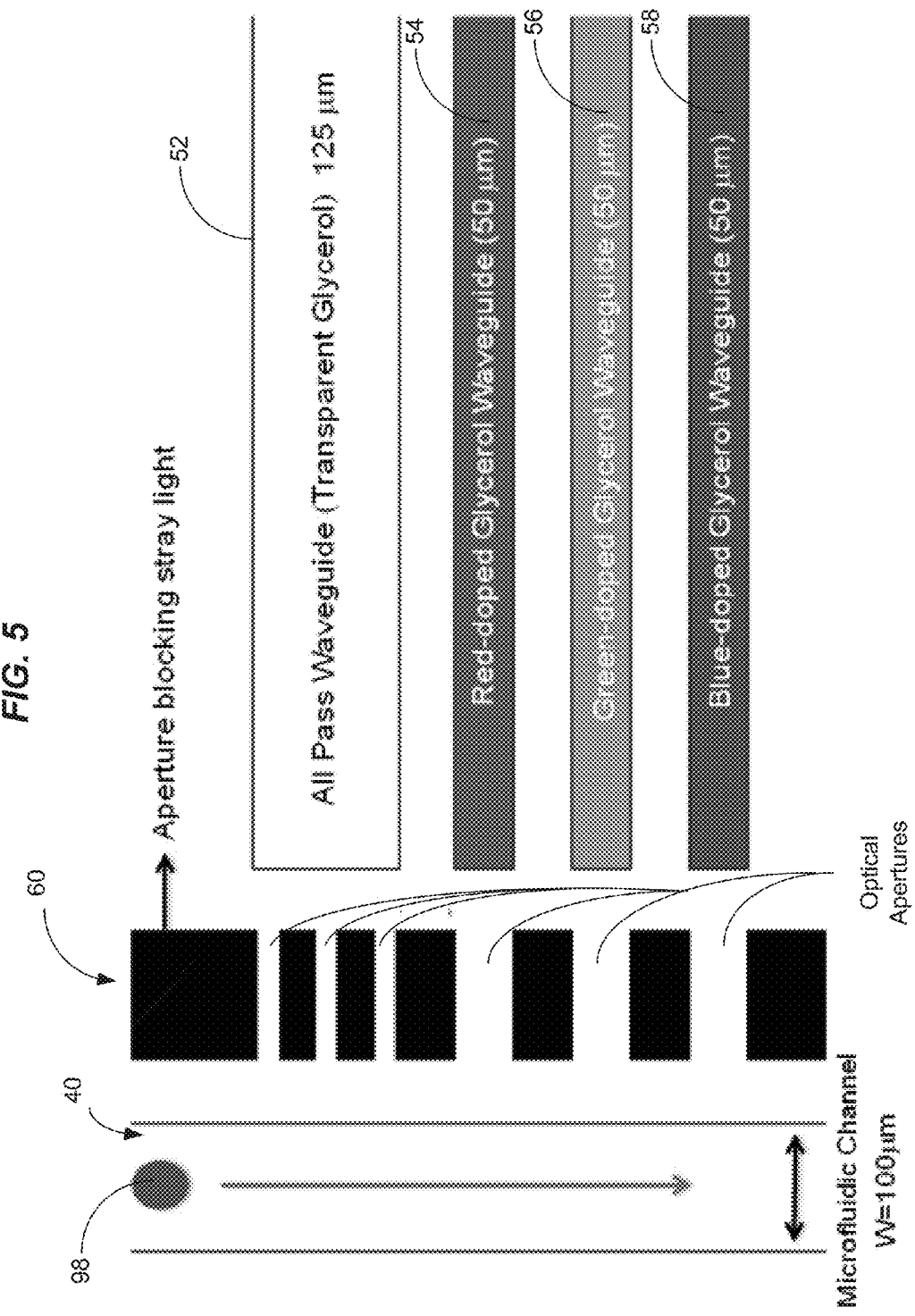
FIG. 5 shows an example of the FACS system with optical filter waveguides and optical apertures.

FIG. 5 shows one example for the design of the FACS device 10 where the encoding structure includes optical aperture structure 60 with multiple optical apertures long the sensing region 40 of the input fluidic channel, and optical waveguides 52, 54, 56 and 58 that receive light from the sensing region 40 via the optical apertures in the structure 60. A particle 98 (e.g., a cell) in the sample fluid flowing through the sensing region 40 emits light that sequentially passes through the optical apertures along the input fluidic channel at different positions at different times. The light received by the waveguides 52, 54, 56 and 58 are collected by the optical detector 14 (e.g., PMT). The waveguide 52 conduct light of all wavelengths emitted by the particles 98. Waveguides 54, 56 and 58 are optical filter waveguides with optical transmission bands that are respectively centered at different center transmission frequencies. The waveguides 54, 56 and 58 produce different filtered optical transmission signals with different optical spectral bands centered at the different center transmission frequencies, e.g., red, green and blue wavelengths and at different times to be received by the optical detector 14. In some implementations, the waveguides 54, 56 and 58 are configured to have spectral overlaps in the optical transmission bands respectively centered at different center transmission frequencies. Therefore, the red waveguide 54 that transmits at a red center wavelength also transmits some light at green wavelengths and some light at blue wavelengths; the green waveguide 56 that transmits at the green center wavelength also transmits some light at red wavelengths and some light at blue wavelengths; and the blue waveguide 58 that transmits at a blue center wavelength also transmits some light at green wavelengths and some light at red wavelengths. Under this design, the signal processing may be based on the overlapping spectral information in each of the different filtered optical transmission signals to improve the signal processing fidelity. For example, the imaging processing by the human visual system based on signals from the red, green and blue color receptors or cone cells in the eye with overlapping spectral ranges can be modeled for the signal processing in the above device.

Figure 6A:
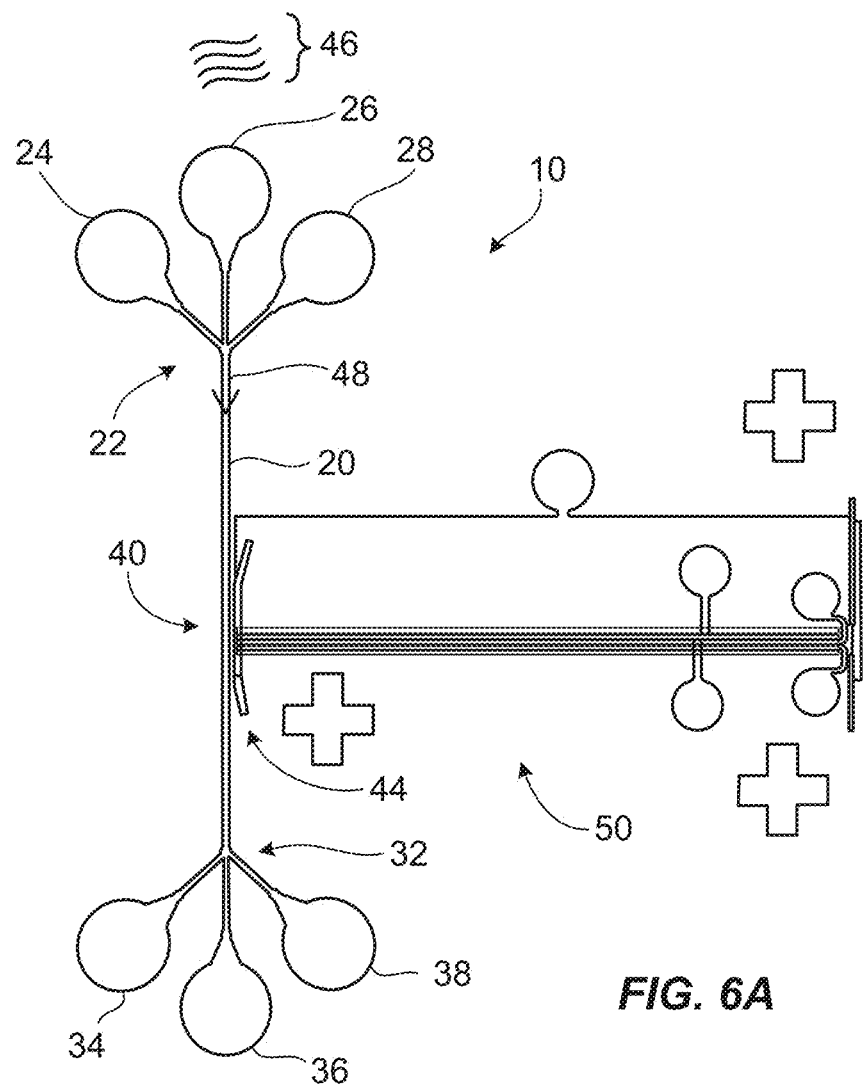
FIG. 6A is a top plan view showing in more detail components of a FACS device employed by the FACS system of FIG. 4.

Turning to FIG. 6A, the components of the FACS device 10 are shown in more detail. As shown, the FACS device 10 includes a microfluidic channel 20 through which cells or other matter of interest, suspended in fluid, pass. The microfluidic channel 20 at a first end 22 is coupled to first, second and third entry orifices 24, 26 and 28, respectively, and at a second end 32 is coupled to first, second and third outlets 34, 36 and 38, respectively. Additionally, at a sampling region 40 of the microfluidic channel 20 intermediate its ends 22, 32, an additional waveguide structure 50 is provided. The additional waveguide structure 50, along with the sampling region 40 of the microfluidic channel 20, is shown in more detail in FIG. 6B. The FACS device 10 can in at least some embodiments be considered disposable because of its low fabrication cost.

In the present embodiment, to improve reliability and reusability of the FACS device 10 as a lab-on-a-chip device, the microfluidic channel 20 is made of polydimethylsiloxane ("PDMS") and, additionally, the PDMS surfaces that are in contact with fluid (e.g., the interior surfaces of the channel) are further coated with a thin, smooth, uniform layer of amorphous Teflon (Teflon AF), particularly a Teflon coating having a lower refractive index (e.g., ~1.31) than that of water (~1.33). Use of the Teflon coating alleviates concerns (which can be present with a variety of PDMS-based microfluidic devices) associated with the porosity and permeation properties of PDMS (which can present concerns especially when dealing with small molecules).

In addition to the above benefits, another benefit of employing the Teflon-coated microfluidic channel 20 is that it facilitates the operation of the microfluidic channel additionally as a low-loss optical waveguide. That is, through the use of the Teflon-coated microfluidic channel 20, in the present embodiment light 46 entering the FACS device 10 from the multimode fiber 6 during operation generally is directed into and guided within the microfludic channel 20 (as indicated by an arrow 48) toward and into the sampling region 40 of the microfluidic channel 20. Upon reaching the sampling region 40, the light 46 impinges the cells or other matter of interest passing through the microfluidic channel and causes fluorescent light to be emitted, some or all of which the enters into the additional waveguide structure 50 arranged along a side 44 of the microfluidic channel 20/sampling region 40.

The above-described implementation of lab-on-a-chip technology is particularly advantageous insofar it constitutes an architecture that allows for multiple detection points along the flow path to enhance sensitivity and suppress noise. In some conventional flow cytometry device architectures, light from a light source (such as an excitation laser source) suffers from power splitting loss. In other words, if a cell (or other subject matter of interest) passes several (e.g., 4) different optical interrogation zones, the excitation laser power may be divided at each of those zones (e.g., divided 4 times) in a manner that results in excessive splitting loss (e.g., 6 dB splitting loss). In contrast, using the above-described embodiment employing the Teflon-coated microfluidic channel 20, the channel conducting the cells (or other subject matter of interest) serves also as the excitation light-guiding waveguide, and consequently it is possible to achieve multi-point optical interrogation as discussed further below. At the same time, the optical intensity of the guided light is lower than a tightly focused laser beam spot to avoid the effect of photo bleaching.

Figure 6B:
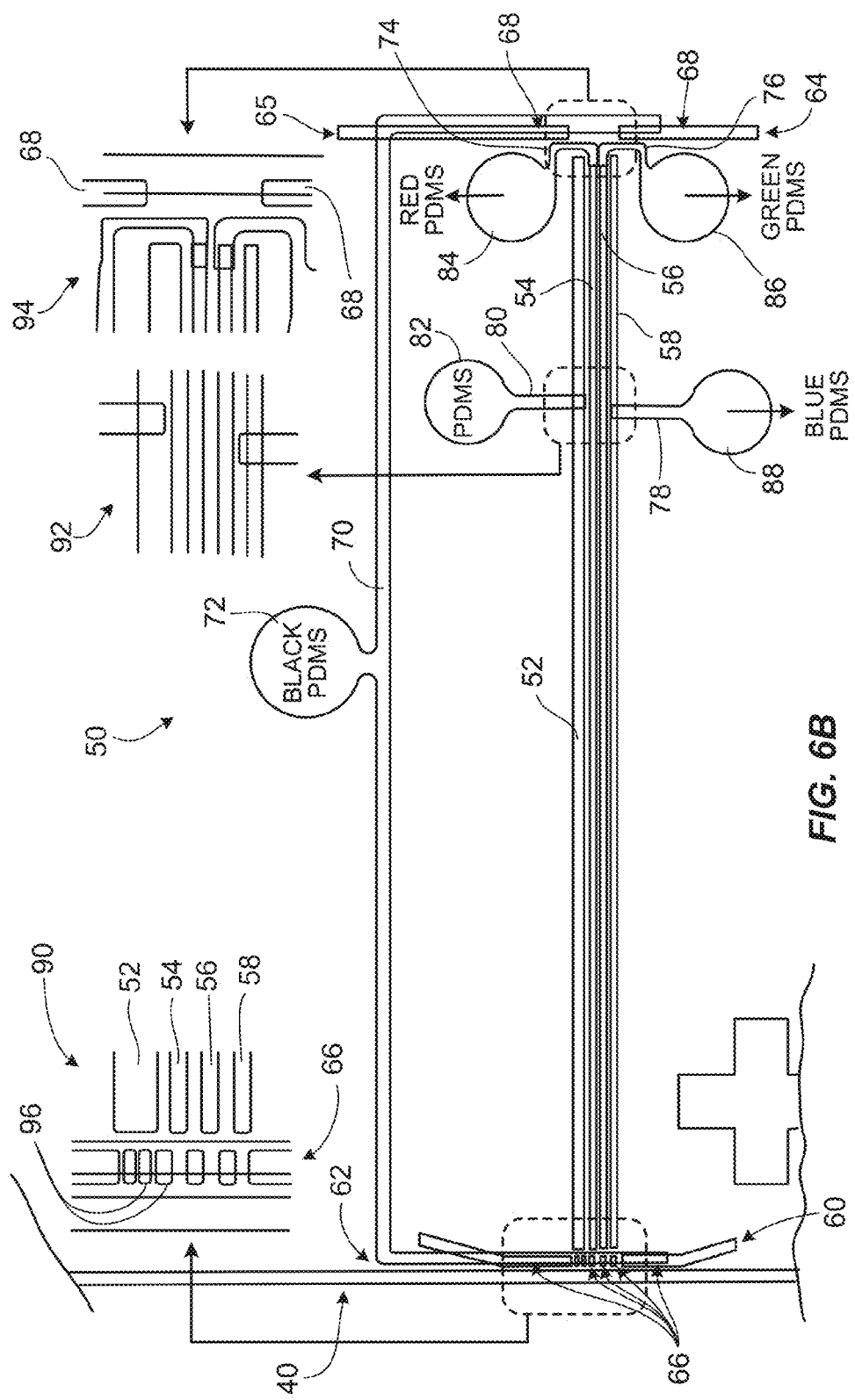
FIG. 6B is an additional view showing portions of the FACS device of FIG. 6A in cut-away in greater detail, which further includes three inset image portions.

Referring additionally to FIG. 6B, the FACS device 10 in the present embodiment achieves multi-point optical interrogation by employing the additional waveguide structure 50 extending away from the sampling region 40 of the microfluidic channel 20. As shown, then additional waveguide structure 50 does not merely include a single waveguide, but rather is shown to include first, second, third and fourth transverse waveguides 52, 54, 56 and 58, respectively. Each of the waveguides 52-58 of the additional waveguide structure 50 extends between a first filter structure 60 positioned at a first end 62 of the additional waveguide structure, which is between the waveguides 52-58 and the sampling region 40, and a second filter structure 64 positioned at a second end 65 of the additional waveguide structure opposite the first end.

Each of the first, second, third and fourth waveguides 52, 54, 56 and 58 has a different respective color. More particularly, the first waveguide 52 is transparent with no particular color (e.g., clear), while the second waveguide 54, third waveguide 56 and fourth waveguide 58 are red, green and blue, respectively. Consequently, while the first waveguide 52 is able to transmit all (or substantially all) components of light within the visible light spectrum (e.g., all light components having wavelengths within the range of about 380 nm to 750 nm, or "white light"), the other waveguides 54, 56, and 58 tend to only transmit red, green and blue light components, respectively, with other colored light components being partially filtered out. Thus, the waveguides 54-58 can also be considered optical filters. As for the first filter structure 60, this structure encompasses several block features 66 that are black or blackened/darkened and that limit the ability of light to proceed form the sampling region 40 to the waveguides 52-58. Further, with respect to the second filter structure 64, this structure also includes block features 68 that are blackened/darkened and that restrict the ability of light to proceed out of the waveguides 52-58 and out of the FACS device 10 toward the PMT 14. The features 66, 68 in particular serve to increase the contrast ratio and reduce crosstalk, and further serve as a beam block for optical isolation.

Typically, it is desirable to take care with optimizing and characterizing the various waveguides 52-58 (and particularly 54-58) to obtain desired operation. To create the red, green and blue waveguides 54-58 as well as the filter structures 60, 64, red, green, blue, and black color dyes are respectively injected into the transverse waveguides and the filter structures. In the present embodiment, the color dyes are oil soluble and can be mixed with high-index (e.g., n=1.42 to 1.46) PDMS to form a colored optical waveguide/filter structures. These high index PDMS prepolymers fill the waveguide channels, which are formed using low-index (n=1.41) PDMS. By properly choosing the color dye or a mixture of different dyes and by calibrating the absorption spectrum, the waveguides 54-58 can each have a respective desired transmission spectrum. In the present embodiment, to cover the maximum number of wavelengths, the center wavelength for the three color filters should occur at around 510 nm, 570 nm, and 640 nm.

In some implementations, each of the red, green and blue (RGB) waveguides (which as mentioned above also can be considered optical filters) 54-58 can be designed to exhibit a gradual change (rather than rapid cutoff) in its transmission characteristics with wavelength. If a single dye is not able to produce the desired spectral response, mixture of dyes may be used. Further, by appropriately coloring/darkening the features 66, 68 of the filter structures 60, 64, and appropriately choosing the shapes and arrangements of those features, light can be appropriately directed from the sampling region 40 to the waveguides 52-58 as well as directed out of the waveguides 52-58 toward the PMT 14. After the color filter design is chosen, optical design software such as ZEMAX (as available from Zemax Development Corporation of Belleview, Wash.) can be used to further design the COST coding FACS system 2.

Referring still to FIG. 6B, in the present embodiment the colored/black dyes are injected into the waveguides 54-58 and filter structures 60, 64 by way of input orifices and channels leading from those input orifices to the waveguides/filter structures. After fluid injection, all PDMS prepolymers are thermally cured to arrive at the waveguides/filter structures. To avoid formation of gaps or voids during curing, the curing is performed in vacuum. More particularly as shown, a black channel 70 leads between a black input orifice 72 and each of the filter structures 60, 64, and thus black dye input at the orifice is able to enter into the filter structures 60, 64 and form the features 66, 68 thereof. Also as shown, red, green and blue channels 74, 76 and 78 respectively lead from respective red, green and blue input orifices 84, 86 and 88, respectively, to the red, green and blue waveguides 54, 56 and 58, respectively, and thus the respective red, green and blue dyes can be injected into the respective waveguides via the respective orifices and respective associated channels. Likewise, a clear channel 80 leads between a clear input orifice 82 and the waveguide 52, allowing for clear dye to be provided to that waveguide.

Additionally, FIG. 6B also includes first, second and third insert images 90, 92 and 94 of FIG. 6B that further illustrate details of the additional waveguide structure 50 and the sampling region 40. More particular, the first inset image 90 shows with more clarity the particular features 66 of the first filter structure 60 as arranged in between the sampling region 40 and the waveguides 52-58. As will be evident from the inset image 90, the features 66 (which again are blackened/darkened to restrict light passage therethrough) are positioned generally in between adjacent ones of the waveguides 52, 54, 56 and 58, with the exception of two small features 96 that are positioned between the sampling region 40 and the waveguide 52. As for the second inset image 92, that image shows in particular the coupling of the channels 80 and 78, respectively, to the waveguide 52 and the waveguide 58, respectively. Further, with respect to the third inset image 94, that image shows the coupling of the channels 74 and 76 respectively to the waveguide 54 and waveguide 56, respectively, as well as the coupling of the channel 70 to the second filter structure 64.

Turning to FIG. 7A, a further schematic illustration is provided of the sampling region 40 and portions of the additional waveguide structure 50, namely, the waveguides 52-58 and the first filter structure 60, including the features 66 of the first filter structure 60, and the second filter structure 64 including the features 68 of the second filter structure 64. FIG. 7A also illustrates the matter of interest, in this example, cells 98 passing through the sampling region 40 of the microfluidic channel 20. As illustrated by different shading of the cells 98, different ones of the cells have been fluorescently labeled with different dyes, such that when those different cells are impinged by the light 46 (as shown in FIG. 6A), the different cells give off different colors of light suitable for transmission by the different ones of the waveguides 54-58 (all of the different colors of light are conducted by the waveguide 52).

It should be understood that, depending upon the embodiment, the additional waveguide structure 50 can be formed by multiple layers of materials. Referring additionally to FIGS. 7B and 7C, respectively, exemplary layers of the additional waveguide structure 50 taken along lines B-B and C-C of FIG. 4A are shown, respectively. FIGS. 7B and 7C in particular show that, in the present embodiment, the channels 70, 74, 76,78 and 80 by which the colored or black PDMS prepolymers are introduced into the waveguides 52-58 and filter structures 60, 64 are at a different layer from the detection plane along which those waveguides/filter structures exist (and along which detected light passes).

More particularly, FIG. 7B shows a cross-sectional view of the additional waveguide structure 50 particularly at the location of the filter structure 60. As shown, the filter structure 60 is formed as a cavity in between a top PDMS layer 102 and a bottom PDMS layer 104. More particularly, the filter structure 60 includes both a tunnel region 110 positioned above the features 66 that particularly serve as the filtering elements. The tunnel region 110, which is positioned above the features 66 (and positioned more within the top PDMS layer 102 than within the bottom PDMS layer 104, within which are positioned the features), connects an input orifice 112 with each of the features so that black dye input at the orifice is able to enter into and form the features 66. It will be observed that the tunnel region 110 and input orifice 112 can be understood to correspond to (and serve the function as) the black channel 70 and black input orifice 72 described above with respect to FIG. 6B, albeit the arrangement of these structures is slightly different in FIG. 7B relative to FIG. 6B.

Similarly, FIG. 7C shows a cross-sectional view of the additional waveguide structure 50 at which are located only the waveguides 52-58 (but not the filter structure 60). As shown, at the particular location shown (corresponding to line C-C of FIG. 7A), all of the waveguides 52-58 are present, positioned in between a top PDMS layer 106 and a bottom PDMS layer 108. Additionally, a tunnel region 114 is shown positioned above the waveguide 52 (that is, more within the top PDMS layer 106 than within the bottom PDMS layer 108, within which are positioned the waveguides 52-58) that connects that waveguide with an input orifice 116. It will be observed that the tunnel region 114 and input orifice 116 can be understood to correspond to (and serve to function as) the channel 80 and input orifice 82 described above with respect to FIG. 6B, albeit the arrangement of these structures is slightly different in FIG. 7C relative to FIG. 6B. It will also be noted that, although corresponding tunnel regions and input orifices can be provided in relation to the waveguides 54-58 (as already discussed with respect to FIG. 6B).

Figures 8A, 8B:
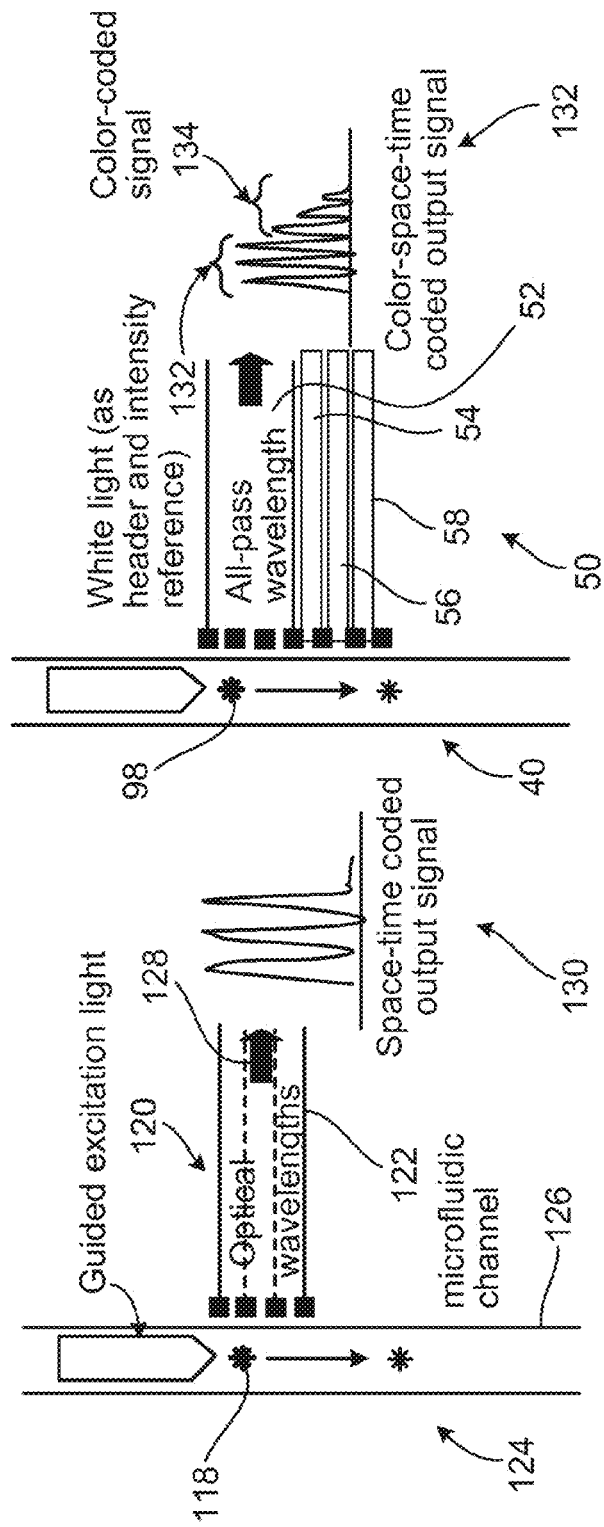
FIG. 8A is a schematic illustration of space-time coding operation of an alternate embodiment of FACS device.
FIG. 8B is a schematic illustration of exemplary COlor-Space-Time (COST) coding operation of the FACS device of FIGS. 6A-7C.

Turning to FIG. 8, operation of FACS systems to perform space-time coding and COST coding is illustrated in greater detail. Referring first to FIG. 8A, a simpler design of a FACS system 120 is shown that only performs time-space coding. As shown, the FACS system 120, in contrast to the FACS system 2 discussed above and further below, only has an array of three clear optical waveguides 122 extending transversely away from the side of the microfluidic channel 126, and that receive fluorescent light given off by cells 118 from a sampling region 124 of a microfluidic channel 126 as filtered by a filter section 128. More particularly, one of the fluorescent cells 118 travels through the channel 126 at a typical speed of 10 cm/s to 100 cm/s. In the present embodiment, the cell 118 is optically excited along its way in a light-fluid co-propagation configuration enabled by the Teflon-coating method discussed above.

The three waveguides 122 of the waveguide array each conduct light away from the microfluidic channel 126 as indicated by an arrow 128, and provide their light output to a single PMT detector. Consequently, as one of the cells 118 travels along the microfluidic channel 126 successively past the waveguides 122 of the waveguide array, three serial peaks separated by the time of travel are detected via the PMT, thus converting the space signal (representing the cell positions) into a space-time coded output signal or time-domain signal 130. Using a digital match filter to match the waveform of the time-domain signal, one can suppress noise and obtain the travel speed of each individual cell, thus establishing the timing for downstream sorting. Further, if one chooses to interrogate a given one of the cells 118 multiple times along its path (e.g. oversampling to enhance the signal-to-noise ratio or to verify whether the cell is sorted to the right channel), it is possible to alter the coding patterns so that the resulting time-domain signal at each point of detection can be extracted using a corresponding match filter.

Turning to FIG. 8B, COST coding improves upon time-space coding by making use of additional transverse waveguides including colored waveguides such as the waveguides 54-58 discussed above. As shown, using the FACS system 2, the output signal provided by the additional waveguide structure 50 to the PMT 14 in response to fluorescent light coming from the sampling region 40 is now a color-space-time (COST) coded signal 132. Again, the waveguide 52 is clear and consequently serves as an "all-pass" waveguide, while the other waveguides 54-58 only pass light of particular colors corresponding to the coloring of those waveguides. Consequently, the COST coded signal 132 includes both a white light signal portion 132 representative of a variety of light components emanating from the waveguide 52, which can be used to establish a reference for overall fluorescence intensity, and also a color-coded signal portion 134 representative of the light of specific colors emanating from the waveguides 54-58. Assuming each fluorescence wavelength has a spectral width of around 30 nm and the three color filter waveguides 54-58 have their maximum transmission wavelengths at 510 nm, 570 nm, and 640 nm, respectively, it is estimated that more than 20 fluorescent wavelengths can be detected using a single detector (e.g., the PMT 14).

Although the waveguide 52 was described above as being a single clear waveguide, as with the array of waveguides 122 shown in FIG. 8A, the waveguide 52 can also include more than one waveguides that form an overall waveguide array. Also, it should be noted that the non-fluorescent dyes in the color filters are not in the path of the excitation laser, so the background fluorescence is not a concern.

The above-described COST technology offers significant benefits in system functionality and cost. Further, assuming particular design constraints, the technology also is consistent with satisfactory device throughput. In particular, assuming the entire transverse waveguide area takes 100 um (in width) and the cell travels at 50 cm/s, the time to pass the optical interrogation zone (that is the zone defined by the outermost edges of the outermost waveguides 52, 58 of the additional waveguide structure 50) within the sampling region 40 is 0.2 ms. This limits the detection throughput to 2,000 to 5,000 cells/s or in the order of 10M cells/hr. Although this can be a satisfactory number for some applications, it still falls short in certain other applications. Therefore, to further increase the throughput, it is further proposed that in certain embodiments in-plane lenses to implement the COST design. In such an integrated lens approach, a lens array creates a series of focal spots that are separated by less than 5 um from each other, thus reducing the total width of the interrogation zone to be around 25 microns. As a result, the time to travel through the COST region becomes less than 50 us. This design can potentially increase the throughput to 20-30K/s or about 100M cell per hour.

Depending upon the embodiment, additional structures can be used to further enhance performance of the FACS and/or other flow cytometry designs described herein. For example, in at least some embodiments, prisms and other structures can be used as described for example, in U.S. patent application Ser. No. 12/152,665 filed on May 14, 2008 entitled "System and Method for Flow Cytometry", U.S. provisional patent application 61/068,198 filed on Mar. 5, 2008 also entitled "System and Method for Flow Cytometry", and further U.S. provisional patent application 60/917,848 filed on May 14, 2007 and entitled "Light Conveying Device", each of which is hereby incorporated by reference herein.

Figure 9:
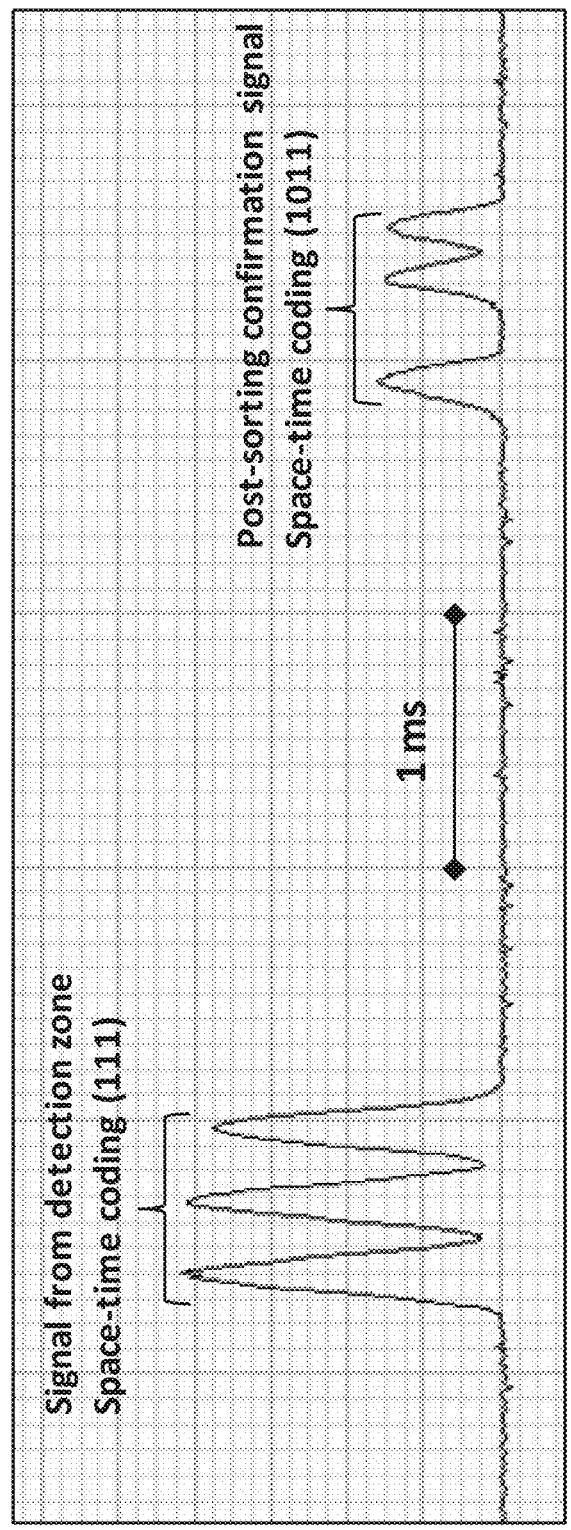
FIG. 9 shows an example of the space-time coding in FIG. 8A.

In FIG. 8A, as the fluorescent cell travels through the channel at a typical speed of 10 cm/s to 100 cm/s, the cell is optically excited along its way in a light-fluid co-propagation configuration. Transverse to the fluidic channel is an array of three apertures that feed their optical transmissions to a single PMT detector. As the cell travels across this array of three apertures, three serial peaks separated by the time of travel are detected, thus converting the space signal (i.e. cell positions) into a time-domain signal. Using a digital match filter to match the waveform of the time-domain signal, the noise in the signal can be suppressed to obtain the travel speed of each individual cell, thus establishing the timing for downstream sorting. If the cell is interrogated multiple times along its path (e.g. oversampling to enhance the signal-to-noise ratio or to verify whether the cell is sorted to the right channel), the coding patterns can be altered so that the resulting time-domain signal at each point of detection can be extracted using a corresponding match filter. FIG. 9 shows that the space-time coded signal (111) at the upstream detection area, followed by another space-time coded signal (1011) downstream after sorting, verifying that the sorting was performed successfully. The first signal (code: 111) represents the detected fluorescence when the bead passes the detection zone. After sorting, the second signal (code: 1011) that is 3.5 ms trailing the first signal indicates that the bead has been correctly switched into the sorting channel.

The multi-parameter on-chip detection and the cell sorting need to function in a well coordinated manner controlled by a real-time electronic system. Sensitivity, latency, and timing jitter are three key issues a good electronic control system needs to address. Sensitivity depends on the quality of the device itself and on the effectiveness of the real-time signal processing capability embedded in the electronic system. Latency is the amount of time required for the algorithms to complete computation. Timing jitter is the variation in latency. The control circuit architecture can be implemented in: (1) analog circuits, (2) microprocessors, or (3) application specific integrated circuit (ASIC). Because of the difficulty in implementing advanced signal processing algorithms in analog circuits and the limited computational power of microprocessors that yields long latency and large timing jitter, the ASIC approach may be implemented for the control circuit. For example, the National Instruments compactRIO system provides a complete embedded system with real-time operating system (RTOS) running on a microprocessor and a field-programmable-gate-array (FPGA), which is basically a highly cost-effective type of ASIC. This system may be used for the control.

The RTOS provides a device driver to access the Ethernet connection chips and the TCP/IP protocol stack for internet communication. This connection is important for data feedback from the compactRIO system and for controlling the real-time hardware. The real-time algorithm can be implemented in the FPGA and the timing jitter is expected to be less than 10 us. In the proposed approach, the electronic control provides the following 3 functions: (1) increasing signal-to-noise ratio (SNR) to improve detection efficiency, (2) instant cell speed estimation to improve sorting accuracy, and (3) sorting signal generation through a waveform generator.

Figure 10:
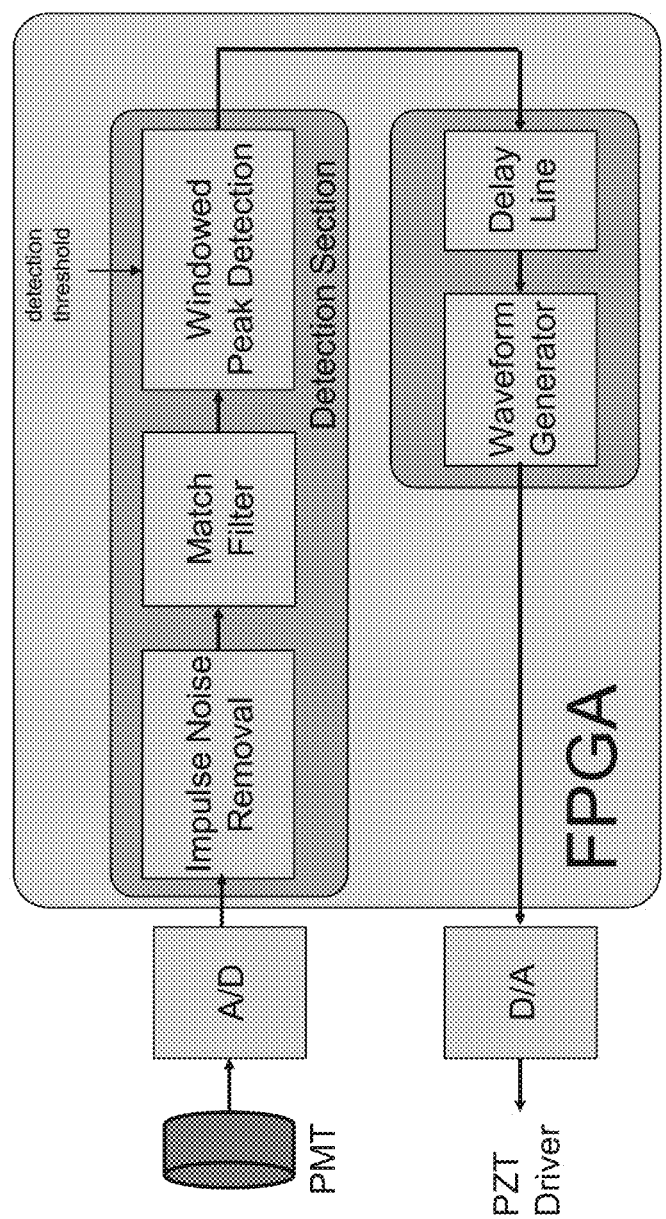
FIG. 10 shows an example of the ASIC architecture of the real-time process control for the FACS device.

The real-time processing control unit shown in FIG. 10 includes the detection section and the control section. In this example, the use of the dedicated hardware for cell detection is to achieve low timing jitter and the control section is to accurately control the timing between the detection of a cell passing and the firing of the actuator with a synthetic waveform to optimize single-cell sorting.

Figure 11:
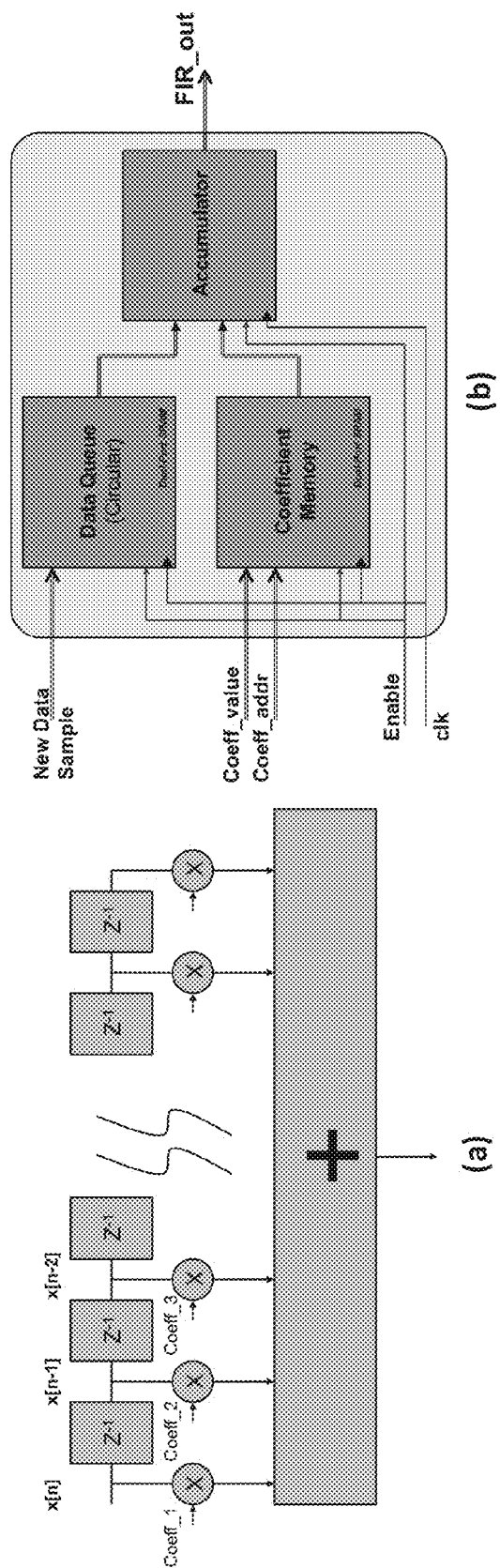
FIG. 11 shows an example of a programmable match filter.

To increase the accuracy of cell detection, three forms of noise that affect the sensitivity can be considered and addressed in designing the detection circuitry: (1) thermal noise of the detection circuit that is nearly white Gaussian noise (WGN), (2) PMT or SPAD dark count noise, and (3) low frequency noise due to laser power fluctuation and stray light. Understanding the characteristics of the noise spectrum, signals can be generated using the aforementioned space-time and COST design so that the signal frequency band has the least overlap with the noise spectrum. Under the WGN condition, the highest S/N ratio can be achieved with the design of match filter, a filter having a response that is the inverse reciprocal of the waveform of the signal. The finite impulse response (FIR) implementation of the match filters is illustrated in FIG. 11.

FIG. 11A shows the basic structure of an FIR filter. This is used as a programmable match filter. FIG. 11B shows the hardware implementation of the FIR filter. This design utilizes a special hardware component—dual-port random access memory (RAM), which is a RAM module that can read and write at the same time. Dual-port RAM is a built-in module in Xilinx FPGA. By utilizing the dual-port RAM, a very high sampling rate filter can be achieved.

In some implementation, real-time cell speed estimation can be implemented for high accuracy single-cell sorting. As the speed of the flowing cells changes, the signal generated from the passing cell changes as well. If the cell speed in the microfluidic channel increases, the signal duration becomes shorter. If the speed of each cell varies in a random fashion, the variation of cell speed can be treated as an additional source of noise. It affects both the S/N ratio and the timing jitter. A more effective match filter can be designed based on the knowledge of the speed of each cell and the match filter can be programmed accordingly. The acquired information of cell speed can also be used to adjust the timing control for high accuracy single-cell sorting.

In the frequency domain analysis, variations in cell speed can be treated as variations of the frequency response of the signal. An increase in cell speed adds more high frequency components to the signal, as illustrated in FIG. 12A. Since the frequency spectra for different cell speeds are different, a filter-bank architecture can be used to estimate the flow speed of each individual cell. An example of such architecture is shown in FIG. 12B. For example, a filter bank of 400 FIR filters can be used to measure, in real time, the flow speed from 1 cm/s to 100 cm/s with an accuracy of 0.25 cm/s. FIG. 12C further shows the process for estimating the cell speed based on outputs of the filters in the filter bank.

Figure 13A:
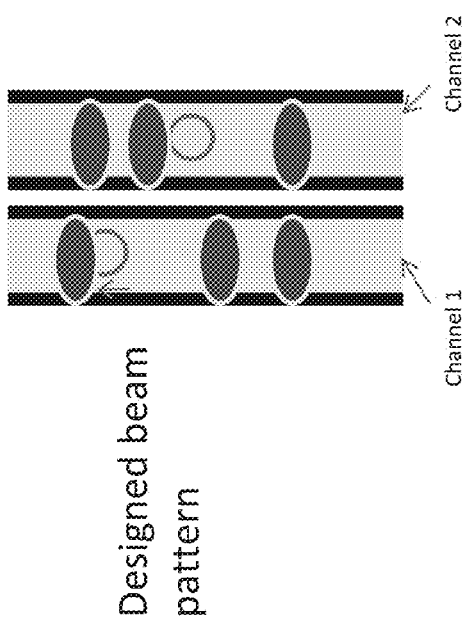
FIGS. 13A and 13B show another example of a signal encoding structure in fluidic channels for an FACS device.
Figure 13B:
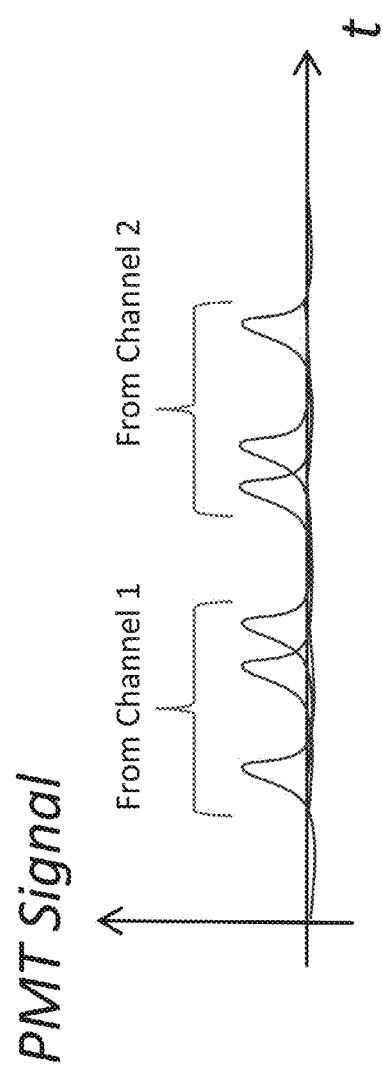

The signal encoding structures used in FIGS. 3A-3C can be in various configurations in addition to the examples shown in FIGS. 5-8B. FIG. 13A, for example, shows another example of a signal encoding structure that uses optical apertures with different inter-aperture spacings to form different beam patterns as the codes. Two fluidic channels with differentg optical aperture designs are illustrated to provide two signal codes. FIG. 13B shows the PMT signals from the two channels in the time domain.

Referring to optical filter design for COST coding in FIGS. 5, 7A, 7B, and 8B, the wide-band filtering for the waveguides 54, 56 and 58 is a mechanism to reduce the number of samples required to differentiate color, e.g. the three filter waveguides 54, 56 and 58 can be used to differentiate 20 different fluorescent wavelengths without using 20 filter waveguides. This is a drastic reduction in cost. The single PMT can be used in connection with the three filter waveguides 54, 56 and 58 because time-multiplexing is performed on the information from different wavelengths into the PMT. For instance, in the example in FIG. 8B, the PMT receives the red light via the waveguide 54 first, then green via the waveguide 56, then blue via the waveguide 58. This time multiplexing is by utilizing flow and waveguides (or spatial filters). Time multiplexing with wideband filtering allows us to have high-throughput color detection.

Figure 14:
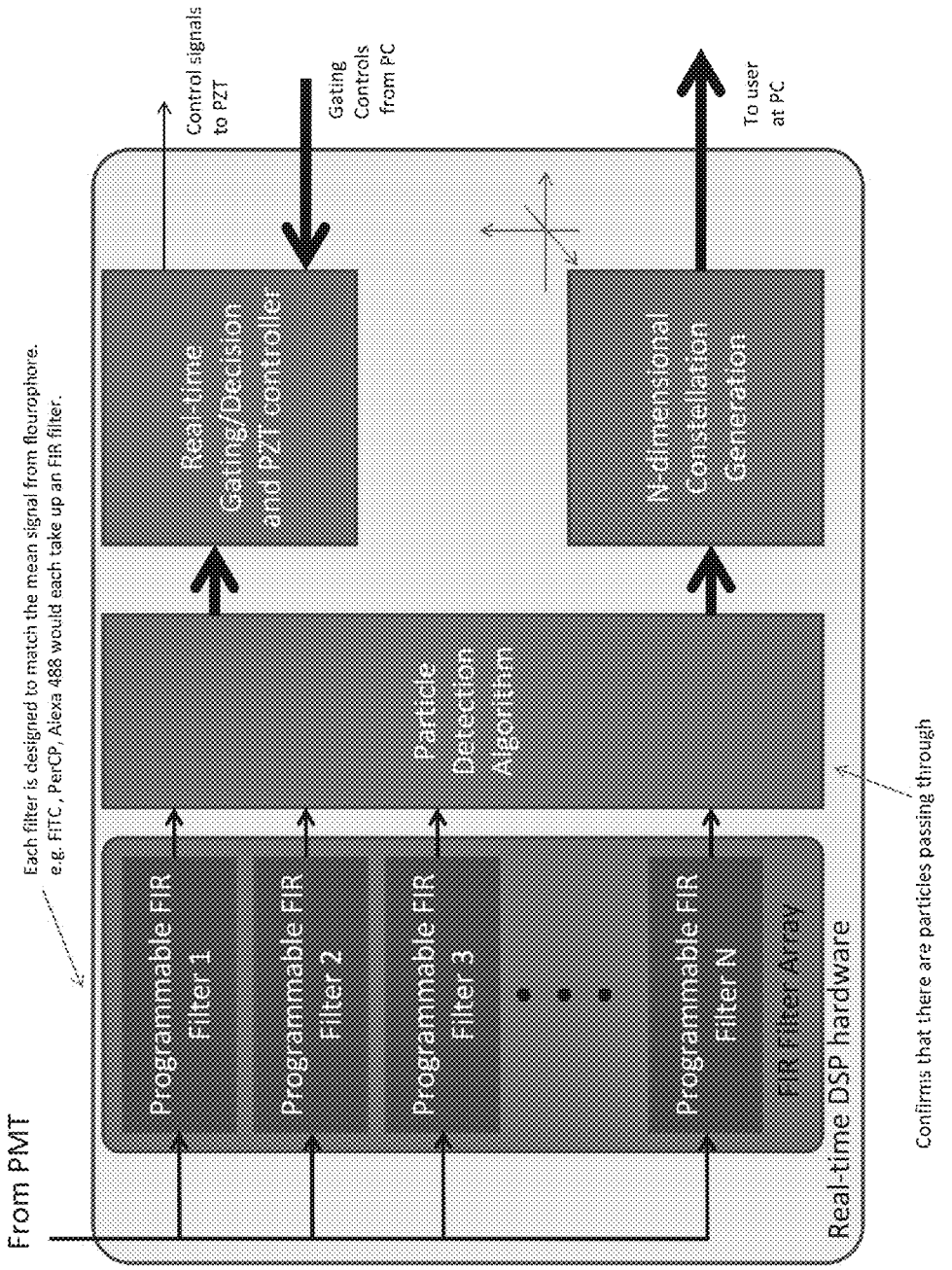
FIG. 14 shows an example of DSP processing block based on programmable FIR filtering bank.

FIG. 14 shows an example of DSP processing block based on programmable FIR filtering bank.

The particle sorting mechanism in flow cytometry devices and systems can be implemented in various configurations. The following sections provide a particle sorter based on a piezoelectric actuator which can be configured to operate with low voltage (typically less than 10 $V_{p-p}$), having low power requirements (typically less than 0.1 mW), and having a fast response time of approximately 0.1-1 msec with particle flow speeds of approximately 1-10 cm/sec. The particle sorting system is operable in a closed loop manner using a spatial filter and processing techniques for determining the presence of a particle by analyzing a light signal over time, which signal is output by a detector.

Referring to FIG. 15, illustrated is a particle sorter 110 for sorting particles in a fluid. The particle sorter 110 includes an input channel 112 connected at an actuation area 114 to a plurality of output channels 116a, 116b, and 116c. Particles flow through the input channel 112 to the actuation area 114, and each particle travels from the actuation area 114 to one of the plurality of output channels 116a, 116b, 116c.

A piezoelectric actuator 118 operates to cause a flow disturbance to fluid in the actuation area 114 in response to a control signal such as a voltage control signal from a controller or driver as illustrated in FIG. 1. For example, as illustrated a positive voltage signal applied to the piezoelectric actuator 118 causes downward bending, and a negative voltage signal causes upward bending. This bending causes a flow disturbance in the actuation area 114, specifically by causing a transverse displacement of fluid (on the order of nanoliters). The flow disturbance directs a particle entering the actuation area along a trajectory to one of the output channels 116a or 116c, which is different than the output channel 16b to which the particle would travel without the flow disturbance. For example, as illustrated in the lower portion of FIG. 15, a positive voltage applied results in downward bending of the piezoelectric actuator 118, causing a flow disturbance in actuation area 114 causing a particle 122 to alter its trajectory and travel to the left and to output channel 116a.

Figure 16A:
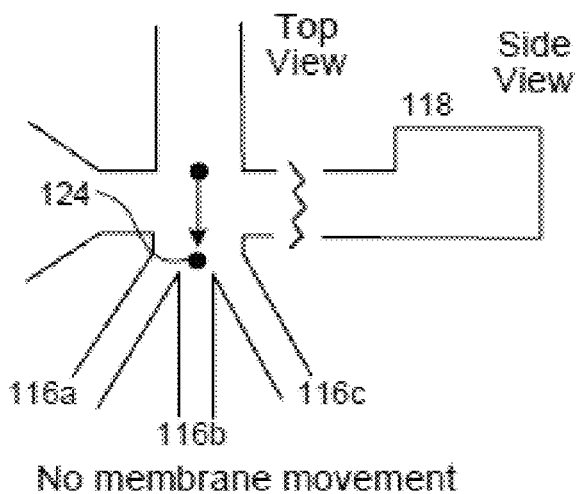
FIGS. 16A, 16B and 16C further illustrate the operation of the particle sorter of FIG. 1.
Figure 16B:
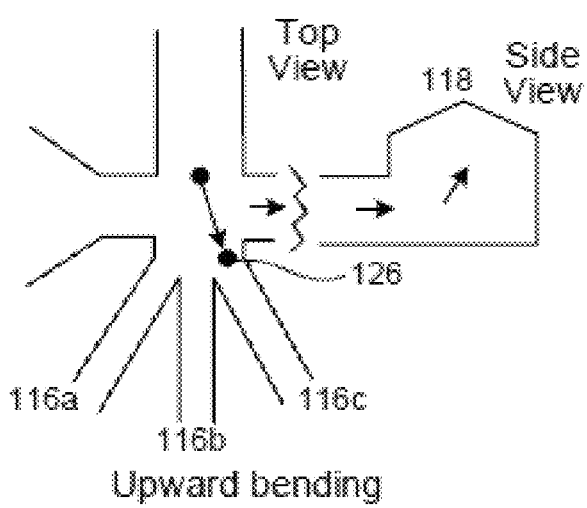
Figure 16C:
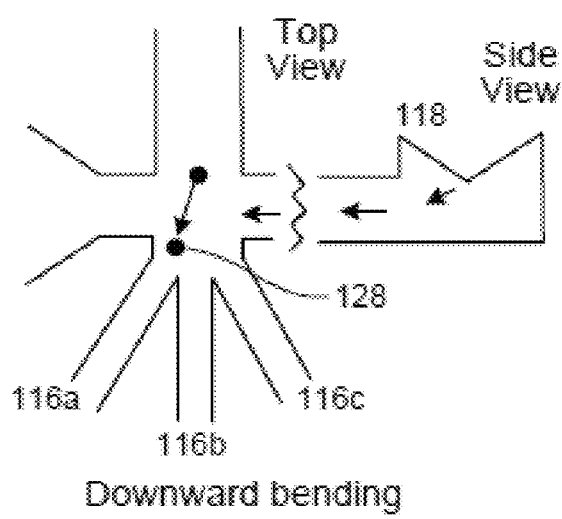

More completely, FIG. 16(a) illustrates travel of a particle 124 when there is no control voltage signal applied, showing travel of the particle to output channel 116b. FIG. 16(b) shows travel of a particle 126 to output channel 116c in response to application of a negative voltage signal. Similarly, FIG. 16(c) shows travel of a particle 128 to output channel 116a in response to application of a positive voltage signal.

FIG. 17 illustrates the simple, low cost fabrication of particle sorter 110, which is accomplished by UV ozone bonding together an etched polydimethylsiloxine (PDMS) substrate 130 and a glass substrate 132. The PDMS substrate 130 has been etched to form the input channel 112, output channels 116a, 116b, 116c, and actuation area 114. Specifically, the PDMS substrate and glass substrate are surface treated in a UV ozone chamber with a lamp output of 28 mW at 254 nm, and bonding occurs as the substrates 130, 132 physically contact each other.

The piezoelectric actuator is formed using a first layer 136 such as stainless steel or copper and a second layer 134 such as lead zirconate titanate. Lead zirconate titanate has a chemical formula of Pb[Zr$_x$Ti$_{1-x}$]O$_3$, where 0<x<1, and is a ceramic perovskite material that shows a marked piezoelectric effect. It is also known as PZT which is an abbreviation of the chemical formula. Contact pads 38 are provided for application of the control signal across the two layers.

The piezoelectric actuator 118 is integrated with the PDMS substrate by first forming a hole in the PDMS substrate, such as by using a 16 mm diameter punch, and then both the PDMS substrate and the piezoelectric actuator 118 are UV ozone treated for another five minutes. The actuator is then aligned and brought into contract with the PDMS substrate 130, and the sorter 10 is then baked at 85 degrees C. for 8 hours.

Figure 18:
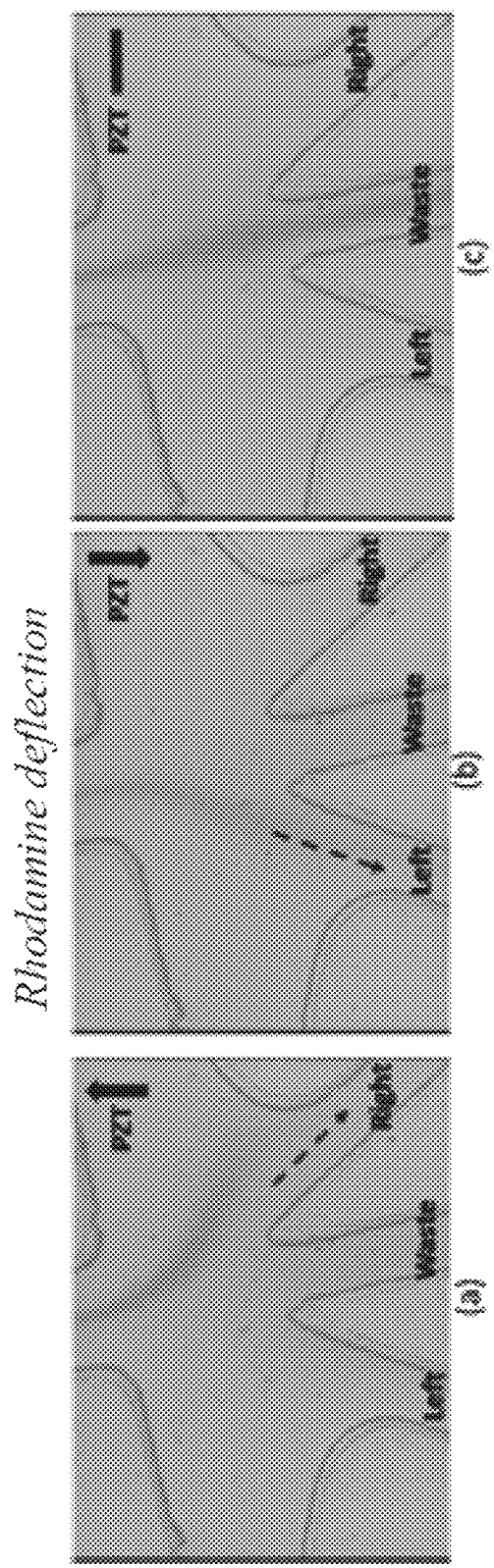
FIG. 18 shows deflection of rhodoamine in the particle sorting system of FIG. 1.

FIG. 18 illustrates the capability of the particle sorter for sorting particles, and shows the deflection of rhodamine caused by the instantaneous finite fluid displacement in the actuation area. In particular, the sorter 110 is mounted on a microscope stage with a high-speed video camera attached for visualization, and the control signal to the piezoelectric actuator 118 is provided by a function generator. Fluid with rhodamine is introduced to the channel, a 250 Hz, 9 V p-p voltage signal provided, and video obtained.

Figure 19:
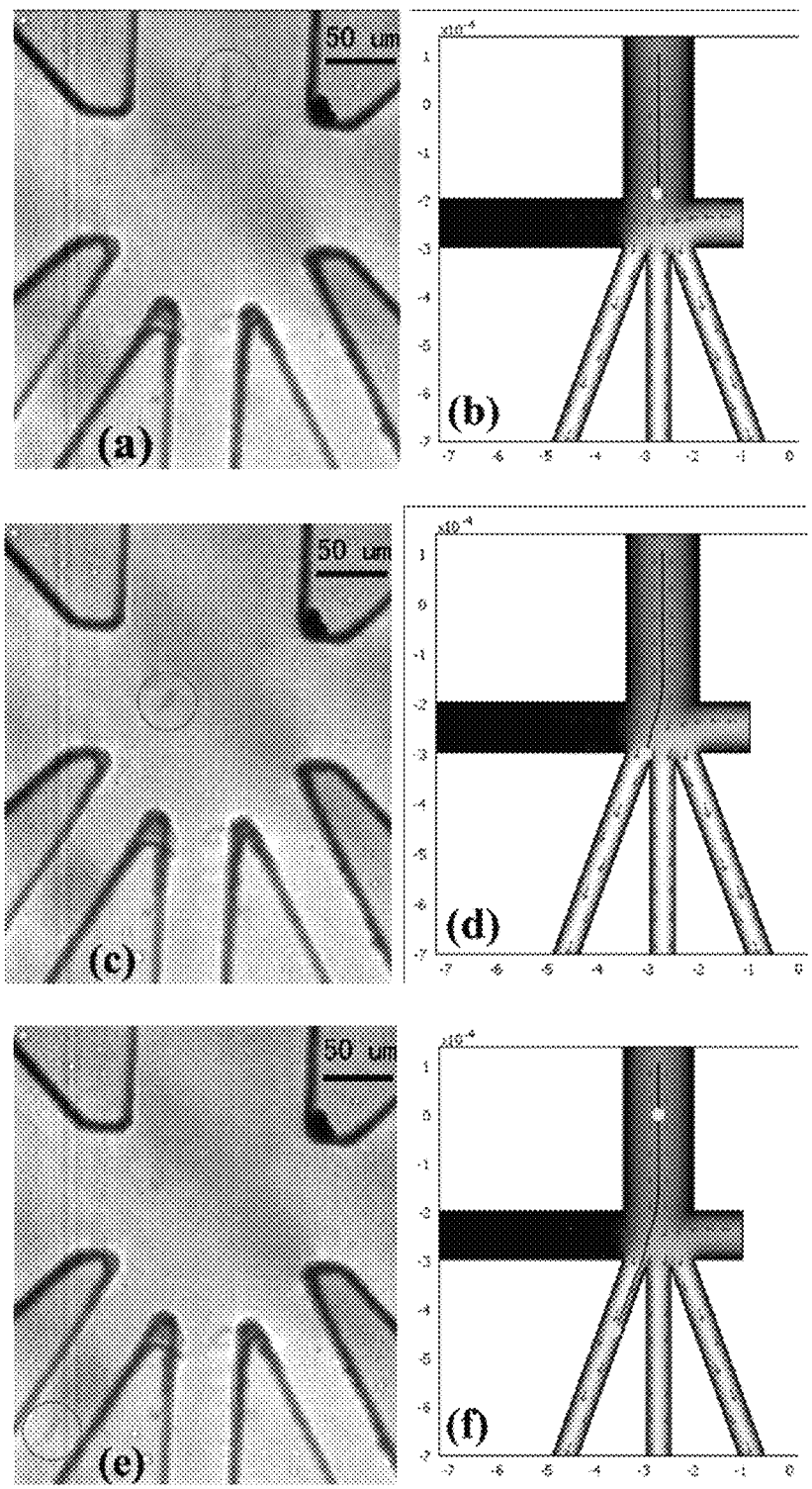
FIG. 19 shows experimental and simulated trajectories of beads.

FIGS. 19(a)-(c) illustrate sequential positions of a polystyrene bead obtained experimentally, and FIGS. 19(d)-(f) illustrate the simulated trajectory of a bead using the incompressible Navier-Stokes equation shown.

Figure 20:
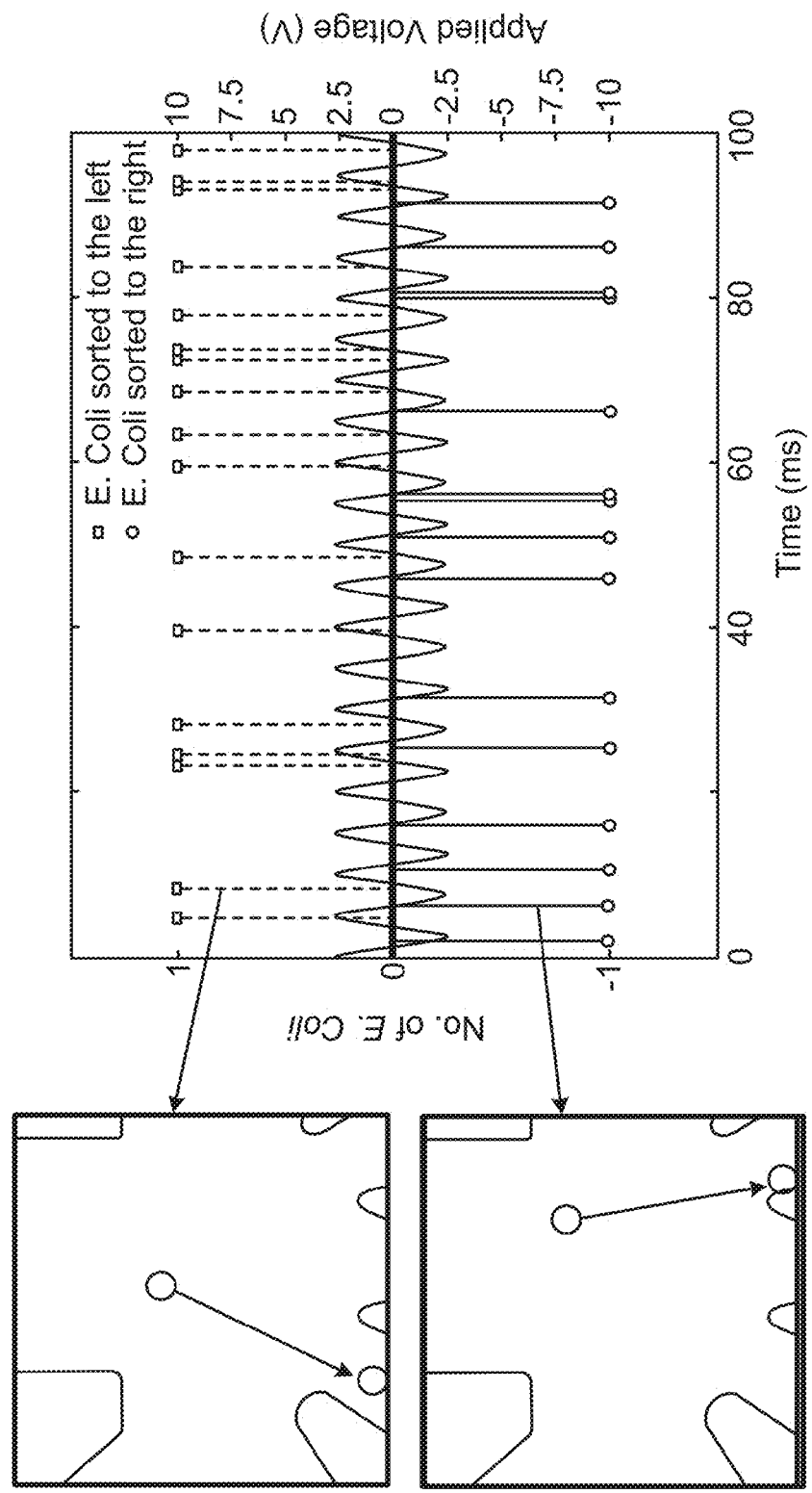
FIG. 20 illustrates the deflection of E. Coli cells subjected to a sinusoidal input voltage as a control signal.

FIG. 20 illustrates the sorting of E. Coli cells subjected to a sinusoidal control voltage signal at 6 Vp-p at 200 Hz.

Figure 21:
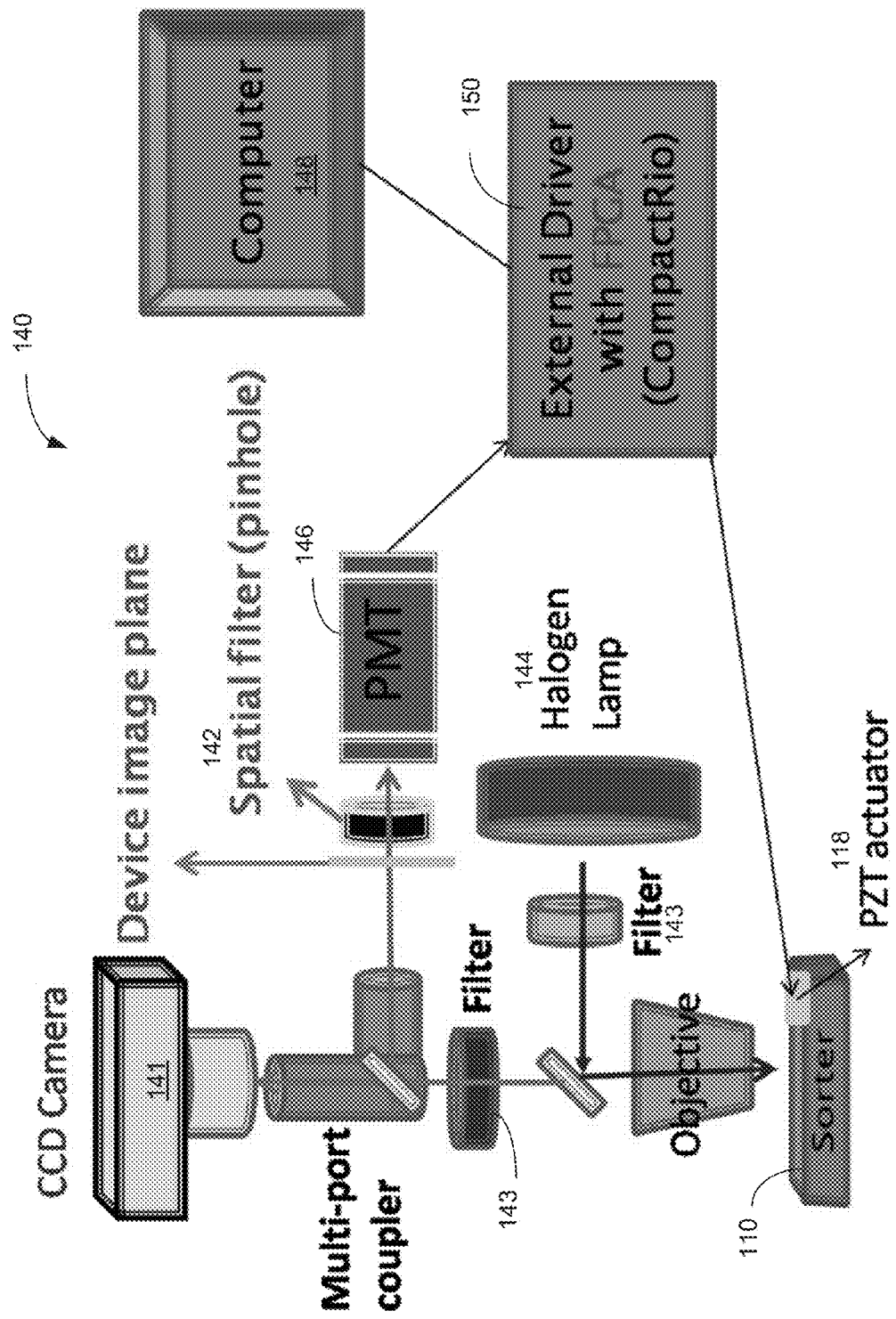
FIG. 21 illustrates a particle sorting system having closed loop control.

FIG. 21 illustrates a closed loop particle sorting system 140, including particle sorter 110, which operates in a closed loop manner to sort particles of interest from other particles in a fluid. A camera 141 for visualization is provided. The particle sorting system also includes a spatial filter 142 (see FIG. 22) having one or more slots and coupled to the input channel, as well as one or more optical filters 143. A light source 144, such as a halogen light, provides input light to the input channel. A detector 146 detects light emitted or scattered from a particle of interest in the input channel, which light has passed through the one or more slots of the spatial filter 142, and provides a detection signal over time. A processor and driver 150, having one or more components implements as a field programmable gate array (FPGA), is in communication with the detector 146 and operates to analyze the detection signal over time. The processor and driver 150 can be in communication with a computer 48 for receiving user input. The processor and driver 150 also generates a presence signal indicative of the presence of a particle of interest passing a predetermined location in the input channel, and generates the control signal for the piezoelectric actuator 118 in response to the presence signal. As described above, the piezoelectric actuator 118 causes a flow disturbance in the actuation area in response to the control signal, wherein the flow disturbance operates to direct a detected particle of interest along a trajectory to one of the plurality of output channels which is different than the output channel to which the particle would travel without the flow disturbance.

Figure 22:
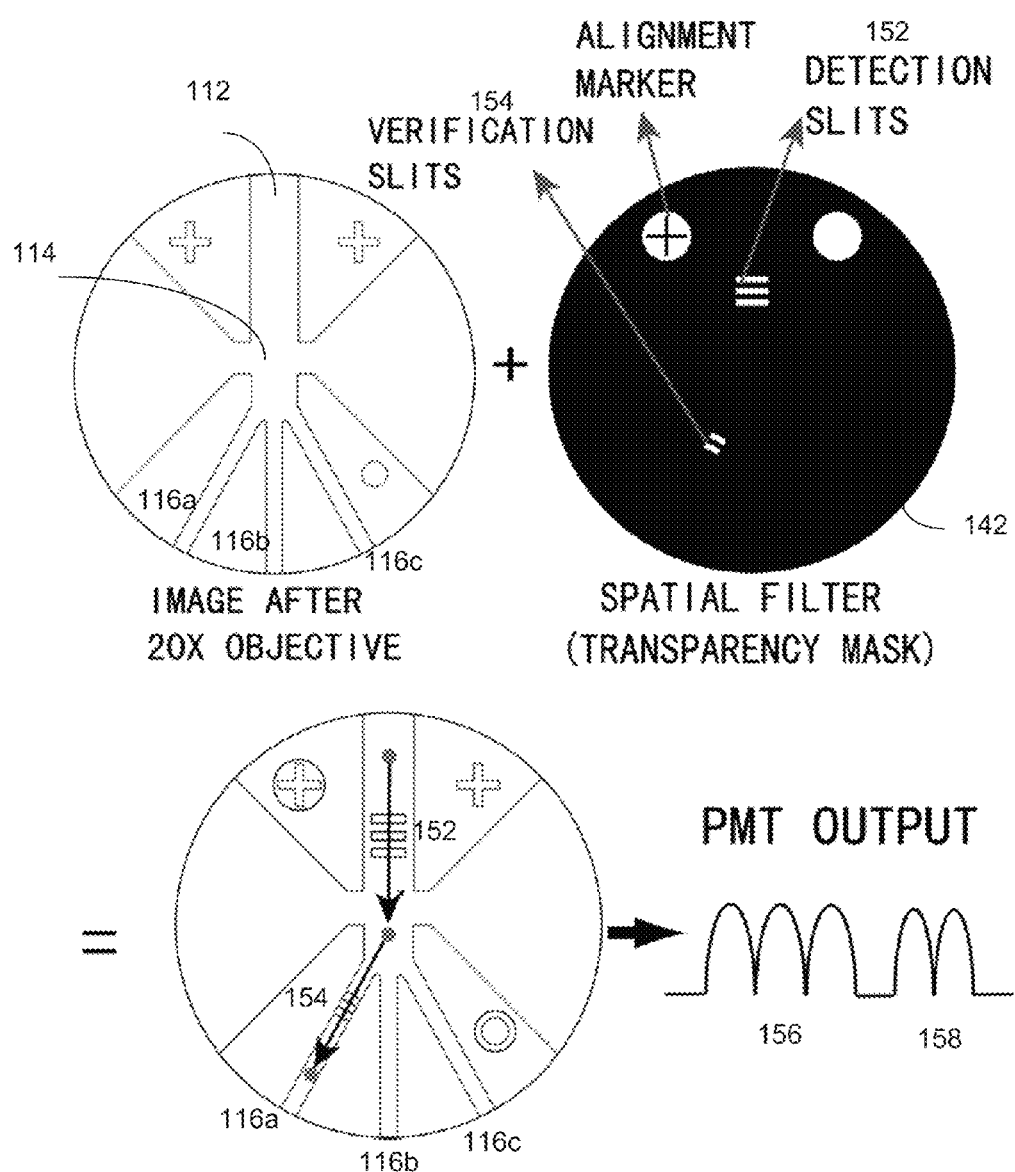
FIG. 22 illustrates a spatial filter for the particle sorting system of FIG. 21.

As shown in FIG. 22, the spatial filter 142 includes a plurality of detection openings or apertures 152 which can be aligned with the input channel 112, and which each allow light from a particle of interest through to the detector 146. The spatial filter 142 can also include a plurality of verification openings 154 aligned with one of the output channels, such as 116a. When a particle of interest travels past the detection openings 152, a signal 156 having an expected pattern (based on flow rate) is produced. This signal can be processed using digital signal processing (DSP) techniques to determine when a particle of interest is present in the input channel. Various DSP techniques can be used, including noise filtering to reduce noise, a finite impulse response filter, or banks of filters. When a particle of interest is present in the input channel, a control signal can be generated, which may need to be delayed so that the flow disturbance occurs when the particle of interest is at an appropriate location in the actuation area 114. Verification that the particle of interest has actually traveled to the desired output channel 116a can be obtained by checking that the signal 158 is obtained following signal 156.

The above spatial filter in FIG. 22 is an exemplary encoding structure in FIGS. 3A and 3B. The spatial filter allows only fluorescence from certain areas in the channel to reach the detector, thus cutting down the background and crosstalk. Each of the specially designed patterns 152 and 154 spatially encodes a fluorescent signal which is transformed into a temporarily encoded signal as the targeted particle/cell travels at a speed. Photolithographic transparency masks (Cad/art services, Inc.) can be used to create spatial filters. The spatially encoded patterns have triple slits (152) and double slits (154). The triple slit pattern (152) encodes the detection signal and the double slit pattern (154) the verification signal from the particles/cells sorted into the designated channel. In the sample spatial filter, the width of the slits is 0.25-0.5 mm, translated to 12.5-25 μm on the microfluidic channels before magnified by a 20× microscope objective. The spatial filter is designed to purposefully coincide with the image plane after magnification. As fluorescent particle passes through detection slits and gets sorted down to the verification slits, the PMT detector is expected to register signals of 3 peaks followed by 2 peaks.

Figure 23:
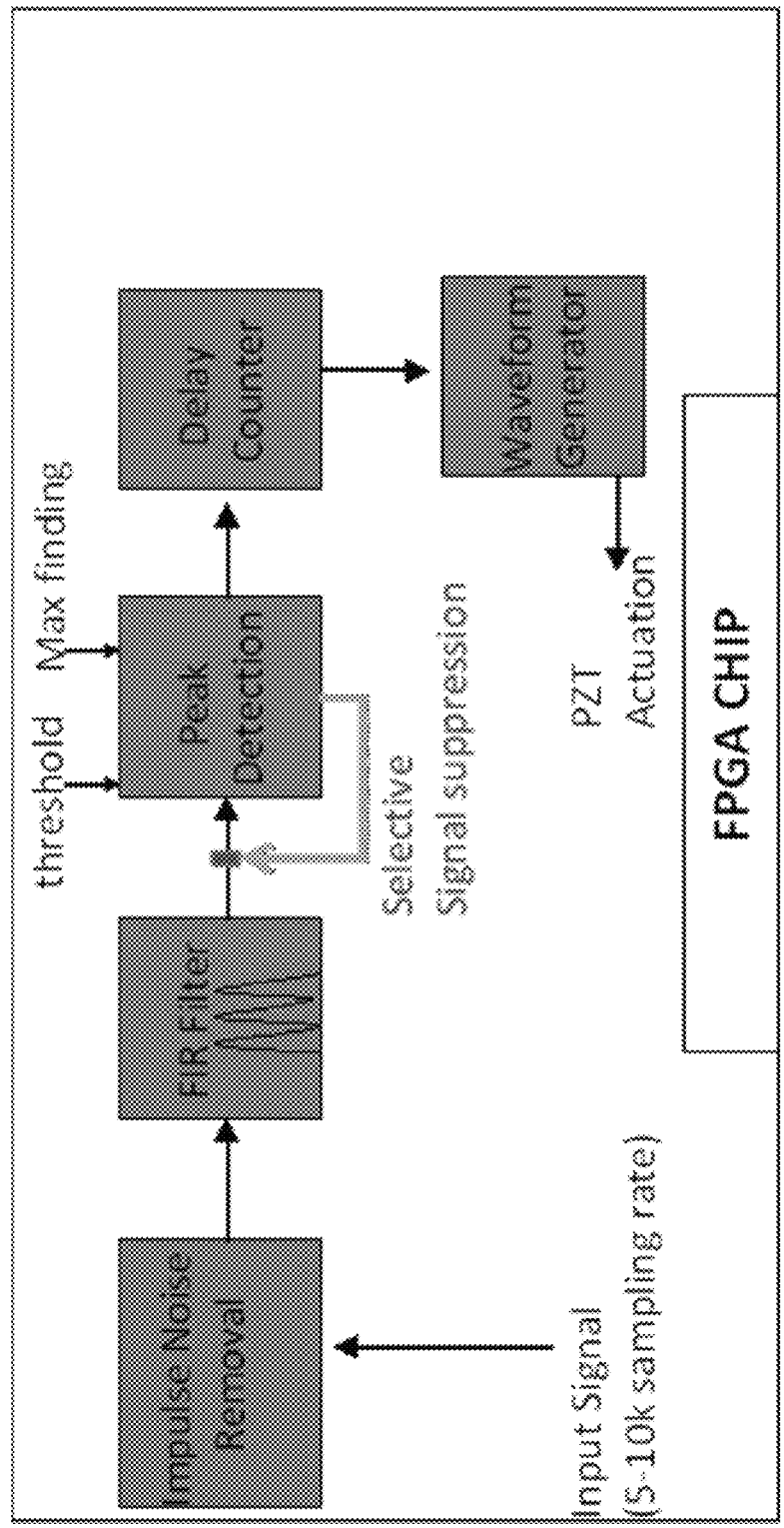
FIG. 23 is a block diagram showing operation of control circuitry for the closed loop system of FIG. 21.
Figure 24:
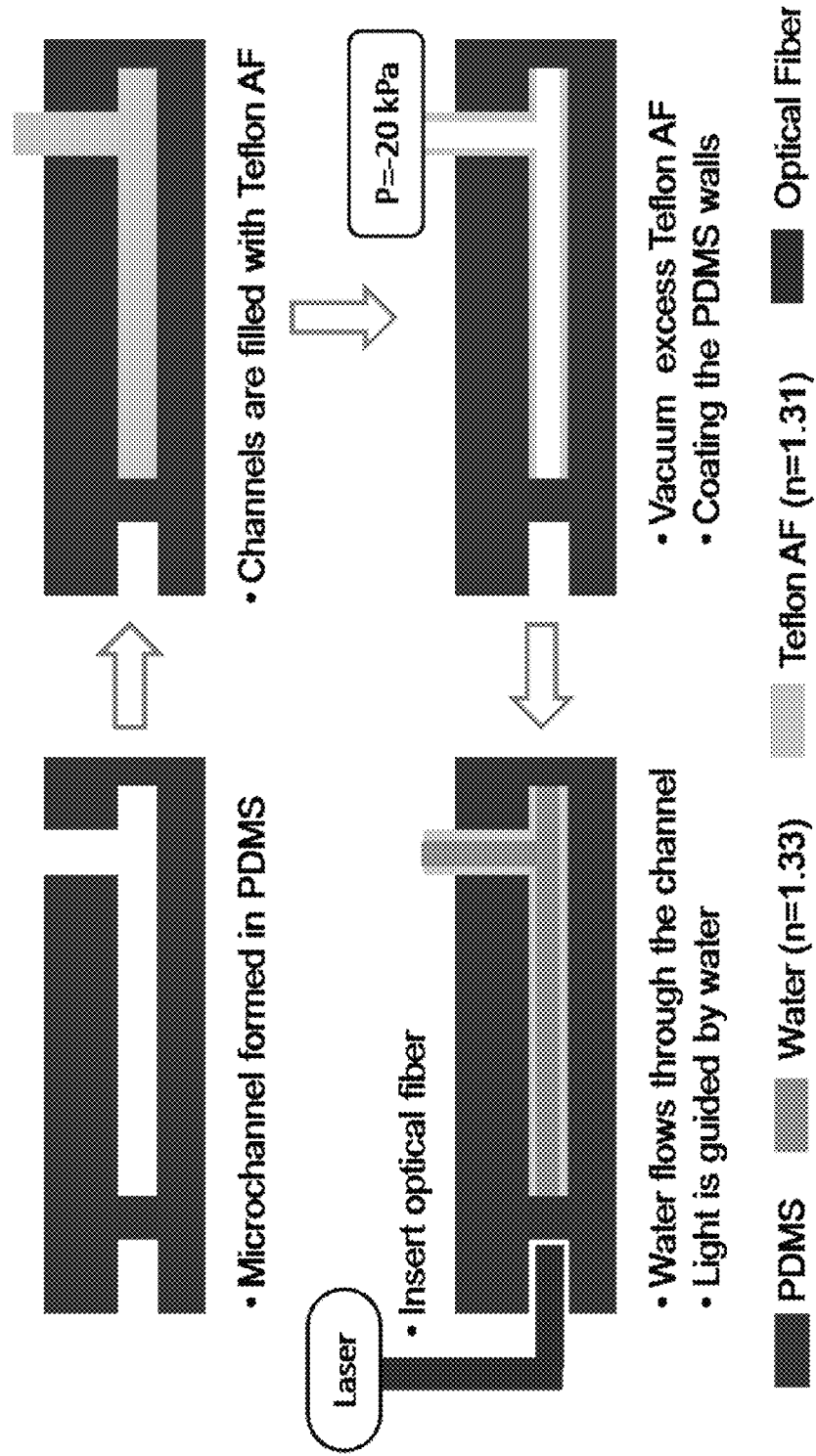
FIG. 24 shows an example of a fabrication process for Teflon AF coated liquid core waveguides. This process reduces the elastic mismatch between PDMS and Teflon AF.

FIG. 23 is a block diagram of one implementation of processor and driver 150, showing the process flow of the electronics control algorithm. The algorithm is programmed into the FPGA chip embedded in the external driver. For example, real-time electronic control is programmed using Labview (National Instrument) with a programmable external driver (CompactRio, NI). The external driver has an independent operating system with an embedded field-programmable gate array (FPGA) chip. The measured jitter of the system is less than 10 μsec. The random high pulse noises of PMT (e.g. caused by sporadic discharge of the device) are removed before running the signal amplification algorithm based on finite impulse response (FIR) filtering. With an FIR matched filter, the signal-to-noise (SNR) ratio can be increased by 18 dB. After SNR enhancement, threshold and search of maximum signal criteria are applied to determine the presence of the detected particle. A signal above threshold indicates that a particle/cell to be sorted is found, triggering the following actions: (a) a delay counter delays the firing of the pulse generator, (b) a preprogrammed output voltage signal is fired to drive the PZT actuator, (c) at certain time period the system is ready to detect the "verification" signal from the sorted sample travelling through the "verification zone", and (d) update record of the sorting efficiency and sorting error. The amount of time delay equals the travel time of the particle from the optical detection zone to the sorting junction. Until the sorted particle is verified, the PZT actuator will not be fired again. This avoids the problem of confusing the verification signal with the signal of particles traveling too close to the particle being sorted.

FIGS. 24-27 illustrate an exemplary method for fabricating optofluidic waveguide that is compatible with polydimethylsiloxane (PDMS). The light path follows the microfluidic channels, an architecture that can maximize detection efficiency and make the most economic use of chip area in many lab-on-chip applications. The PDMS based microfluidic channels are coated with Teflon amorphous fluoropolymers (Teflon AF) which has a lower refractive index (n=1.31) than water (n=1.33) to form a water/Teflon AF optical waveguide. Driven by a vacuum pump, the Teflon AF solution was flowed through the channels, leaving a thin (5 to 15 µm) layer of coating on the channel wall as the cladding layer of optical waveguides. This coating process resolves the limitations of spin-coating processes by reducing the elasticity mismatch between the Teflon AF cladding layer and the PDMS device body. We demonstrate that the resulting optofluidic waveguide confines and guides the laser light through the liquid core channel. Furthermore, the light in such a waveguide can be split when the fluid flow is split. This new method enables highly integrated biosensors such as lab-on-chip flow cytometers and micro-fabricated fluorescence-activated cell sorter (µFACS) with on-chip excitation Optofluidics is an emerging field that integrates microfluidics and optics on the same device to work synergistically. Devices that contain both microfluidic channels and on-chip photonic circuits, such as integrated biochemical sensors, show enhanced functionality and sensitivity and enable significant cost and size reduction. In order to assure that photons and biological samples in the fluid interact most effectively for the highest sensitivity, however, we desire the flexibility to direct and align the paths of light and fluid. In some cases, we need light beams to intersect the fluidic channels to localize the interrogation area. In other cases, we want the light wave and the fluid to share the same path to maximize their interaction. For the latter case, we still lack an effective fabrication method. Due to the fact that most polymers used in lab-on-a-chip devices have a higher index of refraction than water, light traveling in the fluidic channel will not be confined, suffering from high radiation loss. A PDMS-compatible process is provided here for coating microfluidic channels with a layer of low refractive index Teflon AF solution, enabling the water in the fluidic channel to be used as the waveguide's high index core. The Teflon AF coated waveguide works not only for straight fluidic channels but also for split channels. In addition to delivering the light, by Teflon coating the microfluidic channel, a channel is created with low sample adsorption, avoiding a troublesome problem found in many polymer-based microfluidic devices.

Teflon AF is an amorphous fluoropolymer that is chemically stable and optically transparent from UV to IR wavelengths. Unlike other fluoropolymers, Teflon AF has a refractive index (n=1.31) that is lower than the index of water (n=1.33), therefore a Teflon AF coating layer can be used to clad a liquid-core optical waveguide. Light will then be delivered through the same physical path as the fluid flows by total internal reflection (TIR) when the coated channels are filled with water or aqueous solutions. A procedure for coating Teflon AF onto PDMS channel walls is provided here by flowing Teflon AF solution through the micro channel, thereby creating the cladding layer for an optical waveguide along the path of fluid flow. The light introduced to micro channels is confined inside the core of the waveguide (i.e. microfluidic channel) and guided by fluid flowing through the channel.

Microfluidic channels that are 200 µm by 70 µm are fabricated in PDMS. A master mold is lithographically defined on an optically smooth Si wafer using SU-8 50 (MicroChem). Two replicas are created: one replica with microfluidic channels and one replica of an optically smooth blank Si wafer. A solution of 2% 1H,1H,2H,2H-perfluorodecyltriethoxysilane (Sigma Aldrich Inc.) is spin-coated onto PDMS substrates and heated at 110° C. for 10 minutes to promote adhesion between PDMS and the Teflon AF solution. Both PDMS surfaces are then activated for permanent bonding by UV/Ozone treatment (UVO-CLEANER 42, Jelight Inc.) for 3 minutes and bonded together, thus capping the microfluidic channels. A 6% Teflon AF solution (601-S2, DuPont Corp) is flowed into the microfluidic channels. Once they are filled, vacuum (P=−20 kPa) is applied for 20 minutes to remove excess Teflon AF solution from the channels (see FIG. 24.). The balance between the vacuum force and the adhesion to the PDMS channel wall determines the thickness of the cladding layer.

The process results in a smooth channel with a hollow core. The Teflon AF-coated PDMS device is heated to 155° C. for 20 minutes to evaporate the fluoroinert solvent, and then heated further to 175° C. (15° C. above the its glass transition temperature) for 20 minutes to form a smooth Teflon AF layer. This relatively low temperature coating is compatible with PDMS process while significantly reducing the consumption of Teflon solution compared to the spin-coating process. Calculations show that a ~5 µm thick Teflon AF film is necessary to confine the light to the liquid core. In some implementations, the cladding thickness is typically 5 to 15 µm, thick enough to confine and guide light waves. The thickness of the Teflon AF coating layer can be further controlled by adjusting the applied vacuum pressure and concentration of the Teflon AF solution. After slowly cooling the devices to avoid cracking due to thermal mismatch, an optical fiber is inserted into the channel for light coupling. Deionized (DI) water is then introduced into the hollow core to serve as both the sample flow carrier and the core of the optofluidic waveguide.

Figure 25:
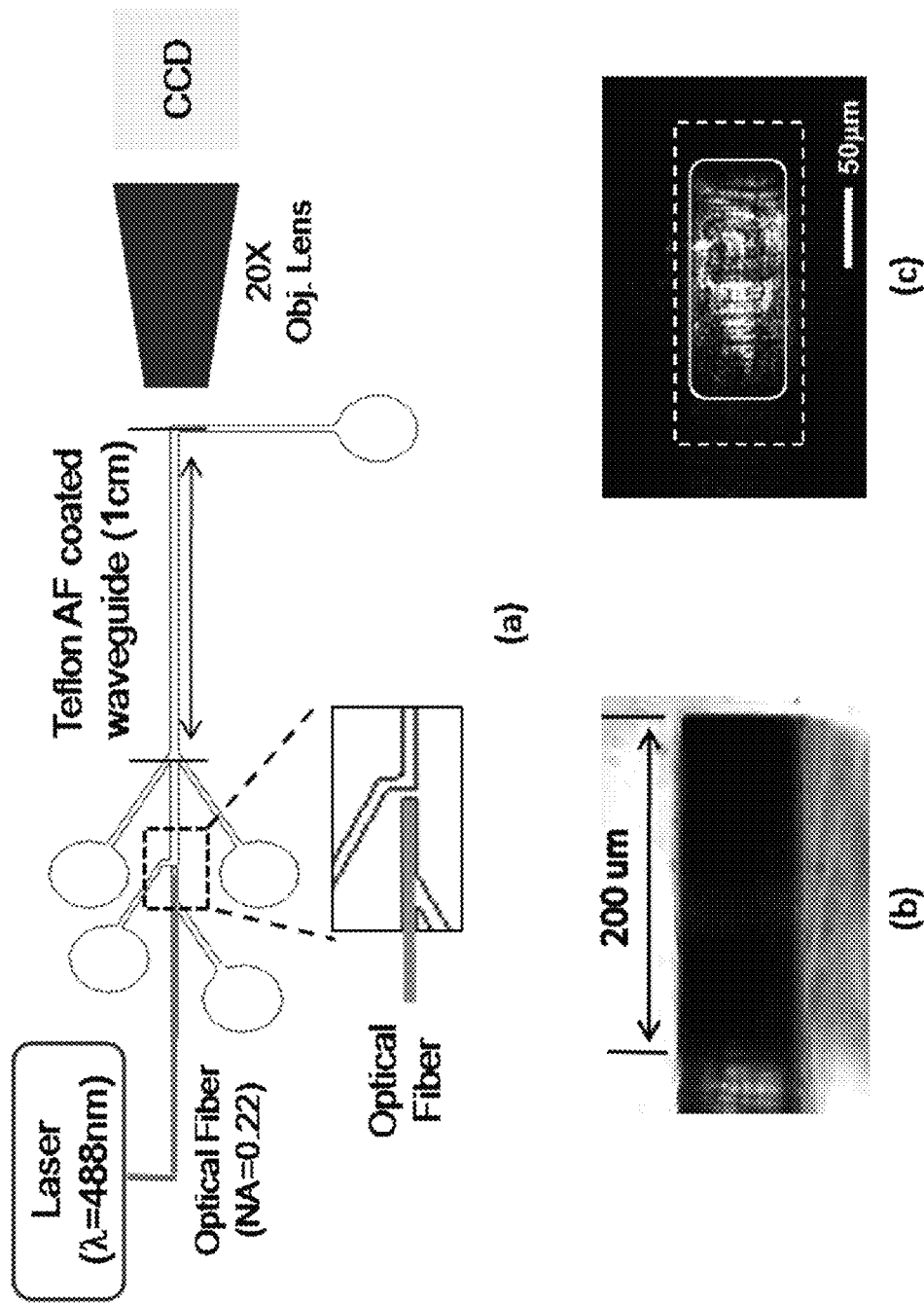
FIG. 25 shows an experimental setup for light output measurement, the cross section of the liquid core waveguide, and the light output from a liquid core waveguide with Teflon AF coating. The dotted box is the perimeter of the channel, and the solid line is the Teflon AF coated core layer.
Figure 26:
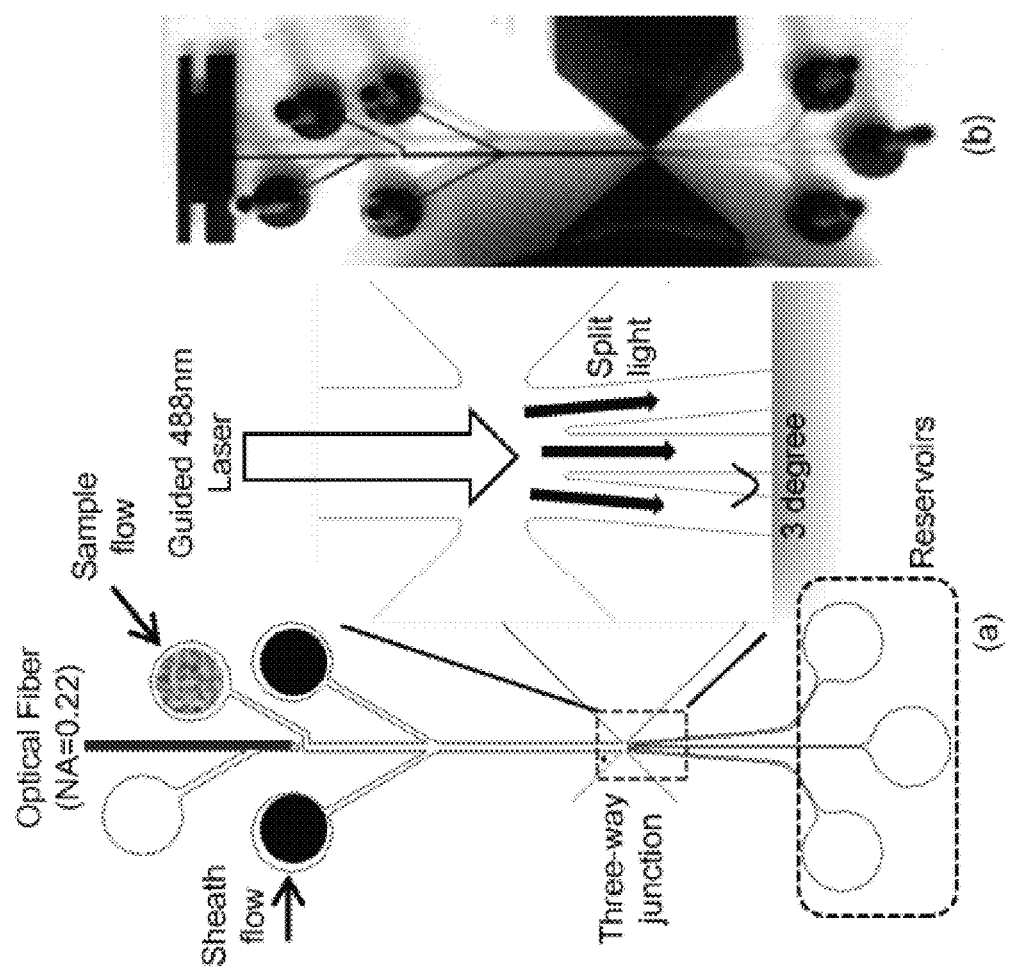
FIG. 26 shows the layout of the device where light can be split and guided at the 3-way junction, and a photograph of the device fabricated in PDMS.

The flowing DI water transports both the suspended samples and the light in the same channel. FIG. 1 illustrates the fabrication process of the Teflon AF coated optofluidic waveguide. The numerical aperture, NA=(ncore2−ncladding2)½, of the liquid core waveguide is 0.23; well-matched to the NA of the input multi-mode fiber (NA=0.22). The cross section of the liquid core waveguide is imaged by a charged coupled device (CCD) at the end of the channel as shown in FIG. 25 (a). FIG. 25 (b) shows the cross section of the fabricated microfluidic channel that is 200 µm by 70 µm. FIG. 25 (c) shows the light output of the optofluidic waveguide when the laser is on. The dotted box shows the wall of the PDMS channel, and the solid line shows the boundary between the Teflon AF cladding layer and the liquid core. It verifies that the light is confined to the liquid core of the optofluidic waveguide by the Teflon AF coating. A waveguide loss of 2.13 dB/cm at 488 nm wavelength is measured. Scattering is the dominant factor compared to light leakage and absorption. With improved smoothness of Teflon AF coating, we believe the waveguide loss can be reduced significantly.

FIG. 26(a) shows the layout of a microfluidic channel which includes a splitting junction, and FIG. 26(b) is a photograph of the device. Laser light (λ=488 nm) is fiber-coupled into the microfluidic channel, in which water flows. Light is guided by the fluid flow, and at the three-way junction, as shown in the enlarged box in FIG. 26(a), the 488 nm light is divided into three paths following the fluid flow towards the channel outlets. In order to demonstrate that light can be split and guided through three channels, we have filled the device with a diluted Rhodamine 6G solution that emits green fluorescence in all directions after absorption of the guided 488 nm light.

Figure 27:
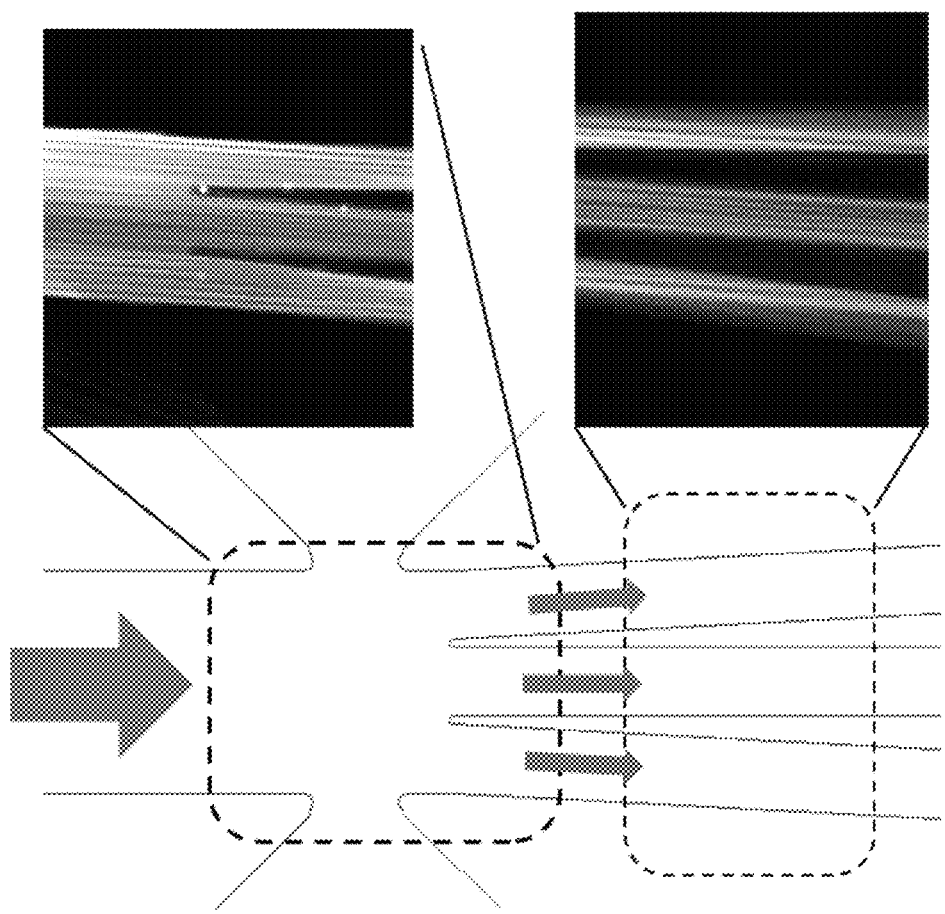
FIG. 27 shows the light emitted by Rhodamine 6G when the fluorescent dye in the fluid is excited by the 488 nm laser light sharing the same paths as the fluid. The 488 nm input light is guided through the entire paths of fluidic channels, even after the three-way split.

As shown in FIG. 27, the light guided from the upstream channel is divided into three split channels separated by 3-degrees. The result demonstrates that the excitation light is split into three channels and that the split light is still guided through the channels. Since the light always traces the fluid flow in which samples are suspended, excitation is performed at all locations, and thus detection can be performed at any position. This unique property provides a very convenient feature for lab-on-a-chip devices. For example, it becomes possible to perform highly sensitive fluorescence detection at multiple locations using only a single light source, imparting a high degree of design flexibility to miniaturized optofluidic devices, for example, lab-on-chip flow cytometers or micro-fabricated fluorescence-activated cell sorter (μFACS).

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

Only a few implementations are disclosed. However, variations and enhancements of the described implementations and other implementations can be made based on what is described and illustrated in this document.

What is claimed is:

1. A particle sorter for sorting particles in a fluid, comprising:
    a substrate;
    a structure formed in the substrate, the structure including an input channel connected at an actuation area to a plurality of output channels, wherein the particles in the fluid flow through the input channel to the actuation area, and each particle travels from the actuation area to one of the plurality of output channels, and
    a piezoelectric actuator coupled to the substrate, the piezoelectric actuator in fluid communication with the actuation area, the piezoelectric actuator configured to deflect in a first direction, in response to a voltage signal, either towards the substrate or away from the substrate for causing a flow displacement along a second direction in the actuation area, the second direction different from the first direction, wherein the flow displacement operates to direct a particle along a trajectory to one of the plurality of output channels which is different than the output channel to which the particle would travel without the flow displacement.

2. The particle sorter of claim 1, wherein the second direction is substantially perpendicular to the first direction.

3. The particle sorter of claim 1, wherein the piezoelectric actuator is offset from a longitudinal axis of the input channel.

4. The particle sorter of claim 1, wherein the structure includes at least one of a polymer substrate, a polydimethylsiloxine (PDMS) substrate, or a glass substrate.

5. The particle sorter of claim 4, wherein the piezoelectric actuator is permanently bonded via UV ozone treatment to the PDMS substrate.

6. The particle sorter of claim 1, wherein the piezoelectric actuator is integrated with the structure.

7. The particle sorter of claim 1, further comprising a driver for generating the voltage signal as a control signal.

8. The particle sorter of claim 1, wherein the voltage signal has a controlled magnitude and frequency.

9. The particle sorter of claim 1, further comprising a detection unit that comprises a bank of filters for detecting a signal from the particle.

10. The particle sorter of claim 1, wherein the piezoelectric actuator includes a contact layer for coupling the piezoelectric actuator to the structure, and further includes a piezoelectric layer for generating a signal to cause the flow disturbance in response to the voltage signal.

11. The particle sorter of claim 10, wherein the contact layer comprises one of copper or stainless steel and the piezoelectric layer is lead zirconate titanate.

12. The particle sorter of claim 1, wherein the particles are a plurality of cells.

13. The particle sorter of claim 12, wherein the plurality of cells are bacterial cells, stem cells, tumor cells, or a combination thereof.

14. The particle sorter of claim 1, wherein the particles are a plurality of beads.

15. The particle sorter of claim 1, further comprising a spatial filter having one or more slots coupled to the input channel, the spatial filter for detecting a signal from the particle.

16. The particle sorter of claim 15, wherein the spatial filter is an optical filter.

17. The particle sorter of claim 1, wherein the input channel and the plurality of output channels are microfluidic channels.

18. The particle sorter of claim 1, further comprising one or more optical filters for detecting a signal from the particle.

19. The particle sorter of claim 18, wherein the one or more optical filters includes one or more optical waveguides.

20. The particle sorter of claim 18, wherein the one or more optical filters are configured to have spectral overlaps in optical transmission bands of the one or more optical filters respectively centered at different center transmission frequencies.

21. The particle sorter of claim 18, further comprising a photomultiplier tube or an avalanche photodiode.

22. The particle sorter of claim 1 further comprising an optical detector for detecting a signal from the particle.

23. The particle sorter of claim 1, further comprising a verification structure coupled to the one of the plurality of output channels, the verification structure configured to produce a branch verification signal upon detection of the particle in the one of the plurality of output channels.

24. The particle sorter of claim 23, the branch verification signal including a branch code that is uniquely associated with the one of the plurality of output channels.

25. The particle sorter of claim 23, wherein the verification structure is a first verification structure of a plurality of verification structures, each verification structure of the plurality of verification structures associated with a different output channel of the plurality of output channels.

26. A particle sorting system for sorting particles of interest from other particles in a fluid, comprising,
    a structure having at least one input channel connected at an actuation area to a plurality of output channels formed on a substrate, wherein the fluid flows through the input channel to the actuation area, and each particle travels from the actuation area to one of the plurality of output channels, a spatial filter having one or more slots and coupled to the input channel, a detection unit comprising a bank of filters to detect a particle of interest at a predetermined location and generate a control signal including a voltage signal in response; and a piezoelectric actuator in fluid communication with the actuation area, the piezoelectric actuator configured to deflect in a first direction, in response to the voltage signal, either towards the substrate or away from the substrate and to cause a flow displacement along a second direction in the actuation area, the second direction different from the first direction, wherein the flow displacement operates to direct a detected particle of interest along a trajectory to one of the plurality of output channels which is different than the output channel to which the particle would travel without the flow displacement.

27. The system of claim 26, further comprising a verification structure coupled to the one of the plurality of output channels, the verification structure configured to produce a branch verification signal upon detection of the particle in the one of the plurality of output channels.

28. The system of claim 27, the branch verification signal including a branch code that is uniquely associated with the one of the plurality of output channels.

29. The particle sorter of claim 27, wherein the verification structure is a first verification structure of a plurality of verification structures, each verification structure of the plurality of verification structures associated with a different output channel of the plurality of output channels.

* * * * *